(12) United States Patent
Sekiguchi et al.

(10) Patent No.: US 8,628,863 B2
(45) Date of Patent: Jan. 14, 2014

(54) INDENOPYRENE COMPOUND AND ORGANIC LIGHT-EMITTING DEVICE USING THE COMPOUND

(75) Inventors: Takeshi Sekiguchi, Tokyo (JP); Hiroshi Tanabe, Yokohama (JP); Hiroki Ohrui, Kawasaki (JP); Masanori Seki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 436 days.

(21) Appl. No.: 13/127,637

(22) PCT Filed: Nov. 6, 2009

(86) PCT No.: PCT/JP2009/069304
§ 371 (c)(1),
(2), (4) Date: May 4, 2011

(87) PCT Pub. No.: WO2010/053210
PCT Pub. Date: May 14, 2010

(65) Prior Publication Data
US 2011/0204354 A1 Aug. 25, 2011

(30) Foreign Application Priority Data
Nov. 6, 2008 (JP) .................................. 2008-285376

(51) Int. Cl.
| | | |
|---|---|---|
| H01L 51/54 | (2006.01) | |
| C07C 25/22 | (2006.01) | |
| C07C 13/62 | (2006.01) | |
| C07C 211/61 | (2006.01) | |
| C07D 213/16 | (2006.01) | |
| C07D 215/06 | (2006.01) | |
| C07D 221/18 | (2006.01) | |
| C07D 239/26 | (2006.01) | |
| C07D 401/04 | (2006.01) | |
| C07D 471/04 | (2006.01) | |

(52) U.S. Cl.
USPC ........... 428/690; 428/917; 313/504; 313/506; 257/40; 544/242; 546/173; 546/276.4; 546/350; 546/75; 546/88; 564/426; 570/129; 570/183; 585/27

(58) Field of Classification Search
None
See application file for complete search history.

(56) References Cited

U.S. PATENT DOCUMENTS

| | | |
|---|---|---|
| 6,849,348 B2 | 2/2005 | Zheng et al. |
| 6,852,429 B1 | 2/2005 | Li et al. |
| 7,233,019 B2 | 6/2007 | Ionkin et al. |
| 2004/0076853 A1 | 4/2004 | Jarikov |

FOREIGN PATENT DOCUMENTS

| | | |
|---|---|---|
| JP | 2005-325097 A | 11/2005 |
| JP | 2006-151845 A | 6/2006 |
| JP | 2007-015961 A | 1/2007 |
| JP | 2007-063285 A | 3/2007 |
| JP | 2007-145799 A | 6/2007 |
| JP | 2007-169182 A | 7/2007 |
| JP | 2007-169581 A | 7/2007 |
| JP | 2007-191603 A | 8/2007 |

OTHER PUBLICATIONS

C.A. Henriques, et al., Characterization of the Coke Formed During o-Xylene Isomerization over Mordenites at Various Temperatures, Journal of Catalysis, 172, 436-445 (1997) Article No. CA971882.
Seung Jun Hwang, et al., Highly Efficent and Versatile Synthesis of Polyarylfluorenes via Pd-Catalyzed C—H Bond Activation, Organic Letters, 2009 vol. 11, No. 20, 4588-4591.

*Primary Examiner* — Dawn L. Garrett
(74) *Attorney, Agent, or Firm* — Canon USA Inc. IP Division

(57) ABSTRACT

Provided is an organic light-emitting device having an optical output with high luminance and high color purity with extremely high efficiency. The organic light-emitting device includes an organic layer between the anode and the cathode, in which one of the anode and the cathode is a transparent electrode or a semi-transparent electrode and at least one layer of the organic layer contains at least one kind of indenopyrene compound having a specific structure.

7 Claims, 4 Drawing Sheets

INDENOPYRENE COMPOUND AND ORGANIC LIGHT-EMITTING DEVICE USING THE COMPOUND

TECHNICAL FIELD

The present invention relates to an indenopyrene compound and an organic light-emitting device using the compound.

BACKGROUND ART

An organic light-emitting device is a device in which a thin film including a fluorescent or phosphorescent organic compound is sandwiched between electrodes. In the organic light-emitting device, electrons and holes are injected from the respective electrodes to generate exciton of the fluorescent or phosphorescent compound, whereby the organic light-emitting device emits light when the exciton returns to a ground state. Recent progress of the organic light-emitting device is remarkable, and the organic light-emitting device is characterized in that the device can be provided with a high luminance at a low voltage applied, a variety of emission wavelengths and high-speed responsiveness and it can be made thin and light weight. From this fact, it is suggested that the organic light-emitting device have potential to find use in a wide variety of applications.

However, in the present circumstances, an optical output with further higher luminance or higher conversion efficiency is needed. Further, when the application of the device to a full-color display or the like is taken into consideration, the emission of blue, green, or red light with good color purity is needed. However, a problem concerning the emission has not been sufficiently solved yet.

As methods for solving the above-mentioned problems, there are disclosed examples, in Japanese Patent Application Laid-Open No. 2007-15961, Japanese Patent Application Laid-Open No. 2007-169581, Japanese Patent Application Laid-Open No. 2007-191603, U.S. Pat. No. 6,852,429, and U.S. Pat. No. 7,233,019, that a pyrene derivative is used as a constituent material of an organic light-emitting device to thereby improve light emitting efficiency, color purity, and the like of the organic light-emitting device. Further, U.S. Pat. No. 6,849,348 discloses an example that a fluorene derivative is used as a constituent material of an organic light-emitting device to thereby improve light-emitting efficiency and the like of the organic light-emitting device.

DISCLOSURE OF THE INVENTION

The present invention has been made with a view to solving the above-mentioned problems of the related art. An object of the present invention is to provide a novel indenopyrene compound. In addition, another object of the present invention is to provide an organic light-emitting device having an optical output with high luminance and high color purity with extremely high efficiency. Further, still another object of the present invention is to provide an organic light-emitting device that can be easily produced at a relatively low cost.

An indenopyrene compound of the present invention is represented by the Formula [1] or [2].

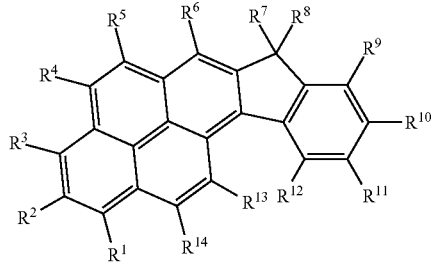

In the formula [1], $R^1$ to $R^{14}$ each independently represents a substituent selected from a hydrogen atom, a substituted or unsubstituted alkyl group, a substituted or unsubstituted alkenyl group, a substituted or unsubstituted alkynyl group, a substituted or unsubstituted aromatic group, a substituted or unsubstituted heterocyclic group, a substituted or unsubstituted fused polycyclic aromatic group, a substituted or unsubstituted fused polycyclic heterocyclic group, a halogen atom, and a substituted or unsubstituted amino group.

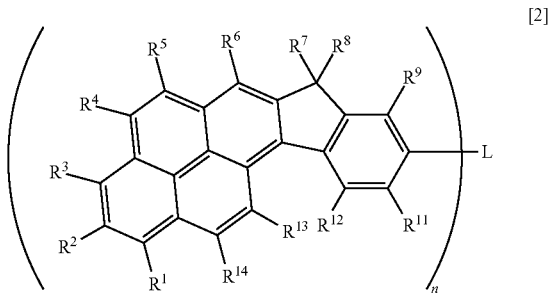

In the formula [2], n represents an integer of from 2 to 4; L represents a single bond or a substituent selected from a substituted or unsubstituted alkylene group, a substituted or unsubstituted alkenylene group, a substituted or unsubstituted alkynylene group, an n-valent substituted or unsubstituted aromatic group, an n-valent substituted or unsubstituted heterocyclic group, an n-valent substituted or unsubstituted fused polycyclic aromatic group, and an n-valent substituted or unsubstituted fused polycyclic heterocyclic group; $R^1$ to $R^9$ and $R^{11}$ to $R^{14}$ each independently represents a substituent selected from a hydrogen atom, a substituted or unsubstituted alkyl group, a substituted or unsubstituted alkenyl group, a substituted or unsubstituted alkynyl group, a substituted or unsubstituted aromatic group, a substituted or unsubstituted heterocyclic group, a substituted or unsubstituted fused polycyclic aromatic group, a substituted or unsubstituted fused polycyclic heterocyclic group, a halogen atom, and a substituted or unsubstituted amino group.

The indenopyrene compound of the present invention is a compound in which oscillator strength of a specific transition is high. Consequently, according to the present invention, there can be provided an organic light-emitting device having an optical output with high luminance and high color purity with extremely high efficiency.

Further features of the present invention will become apparent from the following description of exemplary embodiments with reference to the attached drawings.

BEST MODE FOR CARRYING OUT THE INVENTION

Figure 1:
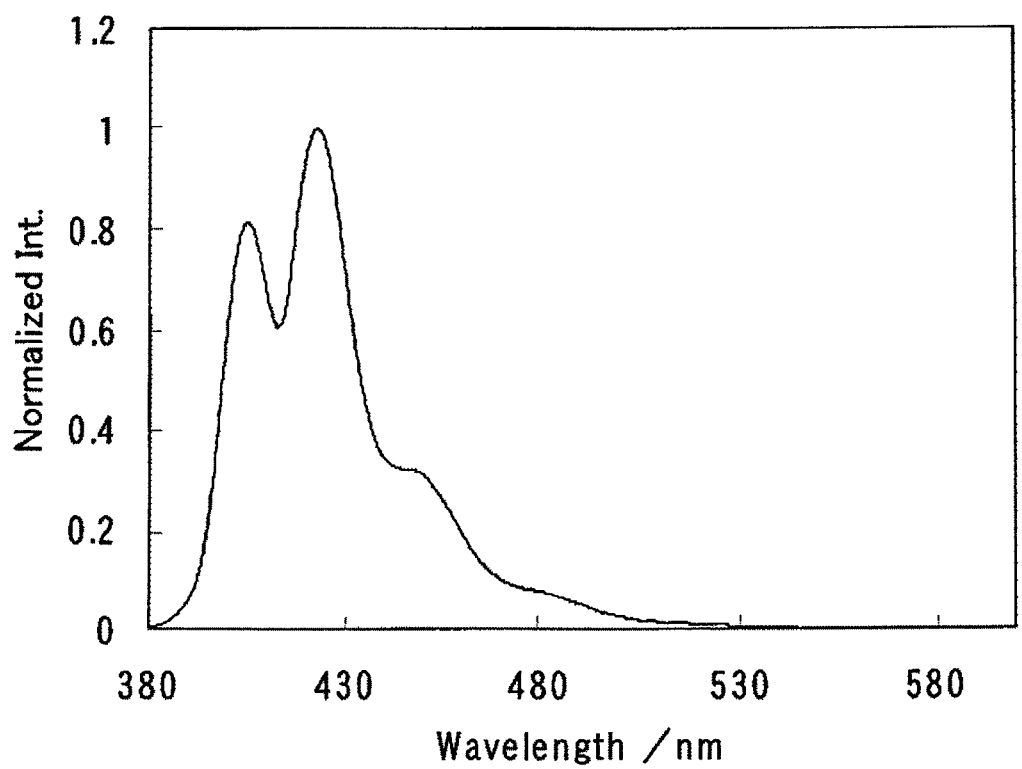
FIG. 1 is a view illustrating the PL spectrum of a toluene solution of Exemplified Compound 3.

Hereinafter, the present invention is described in detail.

First, an indenopyrene compound of the present invention is described.

The indenopyrene compound of the present invention is represented by the Formula [1] or [2].

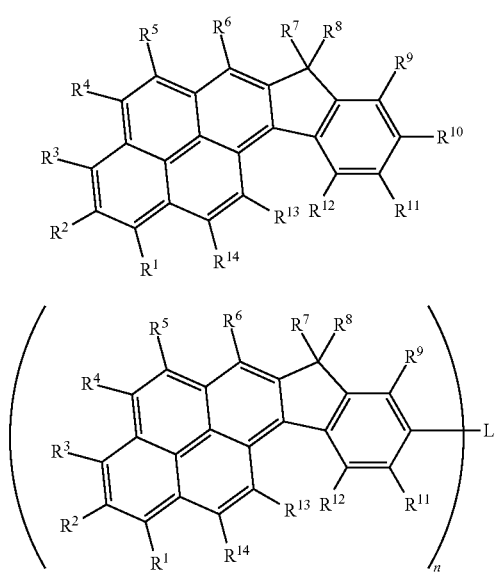

First, the indenopyrene compound represented by the formula [1] (first embodiment) is described.

In the formula [1], $R^1$ to $R^{14}$ each independently represents a substituent selected from a hydrogen atom, a substituted or unsubstituted alkyl group, a substituted or unsubstituted alkenyl group, a substituted or unsubstituted alkynyl group, a substituted or unsubstituted aromatic group, a substituted or unsubstituted heterocyclic group, a substituted or unsubstituted fused polycyclic aromatic group, a substituted or unsubstituted fused polycyclic heterocyclic group, a halogen atom, and a substituted or unsubstituted amino group.

$R^1$, $R^3$ to $R^5$, $R^9$ and $R^{11}$ to $R^{14}$ in the formula [1] each preferably represents a hydrogen atom. $R^2$, $R^6$, $R^7$, and $R^8$ in the formula [1] each preferably represents a hydrogen atom or a substituted or unsubstituted alkyl group. $R^{10}$ in the formula [1] preferably represents a substituted or unsubstituted aromatic group, a substituted or unsubstituted heterocyclic group, a substituted or unsubstituted fused polycyclic aromatic group, a halogen atom, or a substituted or unsubstituted amino group.

Examples of the alkyl group represented by $R^1$ to $R^{14}$ include, but are not limited to, a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, an adamantyl group, a benzyl group, a 2-phenylethyl group, a 2-phenylisopropyl group, a 1-naphthylmethyl group, a 2-naphthylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, and a 4-bromobenzyl group.

Examples of the alkenyl group represented by $R^1$ to $R^{14}$ include, but are not limited to, a vinyl group, a 1-propenyl group, a 2-propenyl group, a 1-butenyl group, a 2-butenyl group, and a 3-butenyl group.

Examples of the alkynyl group represented by $R^1$ to $R^{14}$ include, but are not limited to, an ethynyl group, a 1-propynyl group, a 2-propynyl group, a 1-butynyl group, a 2-butynyl group, and a 3-butynyl group.

Examples of the aromatic group represented by $R^1$ to $R^{14}$ include, but are not limited to, a phenyl group, a biphenyl group, and a terphenyl group.

Examples of the heterocyclic group represented by $R^1$ to $R^{14}$ include, but are not limited to, a pyridyl group, a pyrrolyl group, a bipyridyl group, a methylpyridyl group, a pyrimidinyl group, a pyrazinyl group, a pyridazinyl group, a terpyrrolyl group, a thienyl group, a terthienyl group, a propylthienyl group, a furyl group, an oxazolyl group, an oxadiazolyl group, a thiazolyl group, and a thiadiazolyl group.

Examples of the fused polycyclic aromatic group represented by $R^1$ to $R^{14}$ include, but are not limited to, a naphthyl group, an acenaphthyrenyl group, an anthryl group, a phenanthryl group, a pyrenyl group, an acephenanthrylenyl group, an aceanthrylenyl group, a chrysenyl group, a dibenzochrysenyl group, a benzoanthryl group, a dibenzoanthryl group, a naphthacenyl group, a picenyl group, a pentacenyl group, a fluorenyl group, a 9,9-dihydroanthryl group, a triphenylenyl group, a perylenyl group, a fluoranthenyl group, a benzofluoranthenyl group, a benzophenanthryl group, and substituents derived from fused polycyclic aromatic compounds represented below.

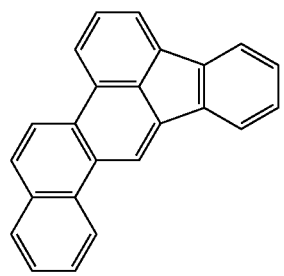

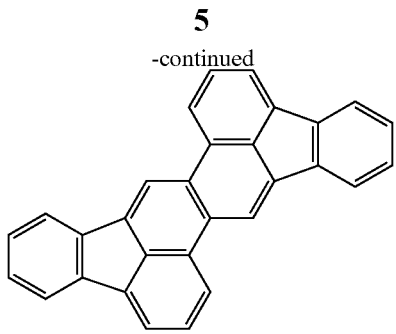

Examples of the fused polycyclic heterocyclic group represented by $R^1$ to $R^{14}$ include, but are not limited to, a quinolyl group, an isoquinolyl group, a benzothienyl group, a dibenzothienyl group, a benzofuryl group, an isobenzofuryl group, a dibenzofuryl group, a quinoxalinyl group, a naphthridinyl group, a quinazolinyl group, a phenantridinyl group, a phenanthrolyl group, an indolidinyl group, a phenadinyl group, a carbazolyl group, an acridinyl group, a diazafluorenyl group, an azafluorenyl group, an azafluoranthenyl group, and an azabenzofluoranthenyl group.

Examples of the halogen atom represented by $R^1$ to $R^{14}$ include, but are not limited to, fluorine, chlorine, bromine, and iodine.

Examples of the substituted or unsubstituted amino group represented by $R^1$ to $R^{14}$ include, but are not limited to, an amino group, a dimethylamino group, a diethylamino group, a diphenylamino group, a di(9H-fluorene-2-yl)amino group, and a bis(9,9-dimethyl-9H-fluorene-2-yl)amino group.

Examples of the substituent that the alkyl group, alkenyl group, alkynyl group, aromatic group, heterocyclic group, fused polycyclic aromatic group, and fused polycyclic heterocyclic group may have include, but are not limited to, alkyl groups such as a methyl group, an ethyl group, a propyl group, and a tert-butyl group; aromatic groups such as a phenyl group and a biphenyl group; heterocyclic groups such as a thienyl group, a pyrrolyl group, and a pyridyl group; a 9,9-dimethyl-9H-fluorenyl group; 9,9,9',9'-tetramethyl-9H-9H'-2,2'-bifluorenyl group; halogen atoms such fluorine, chlorine, bromine, and iodine; a cyano group; and a nitro group.

Next, preferred examples of the first embodiment are described below.

As a first preferred example of the first embodiment, a compound satisfying the following items (a) to (c) can be exemplified: (a) $R^1$, $R^3$ to $R^5$, $R^9$, $R^{11}$, $R^{13}$, and $R^{14}$ each represents a hydrogen atom; (b) $R^2$, $R^6$, $R^7$, $R^8$ and $R^{12}$ each represents a hydrogen atom or a substituted or unsubstituted alkyl group; and (c) $R^{10}$ represents a hydrogen atom, a substituted or unsubstituted alkyl group, a halogen atom, or a substituted or unsubstituted amino group.

Specific examples of the first preferred example are shown below. However, the present invention is not limited thereto.

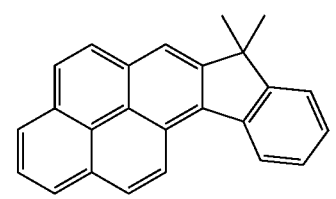

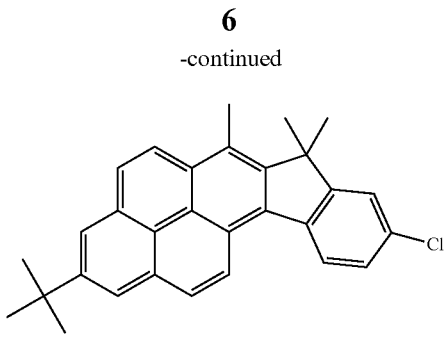

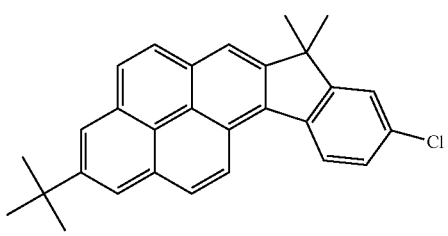

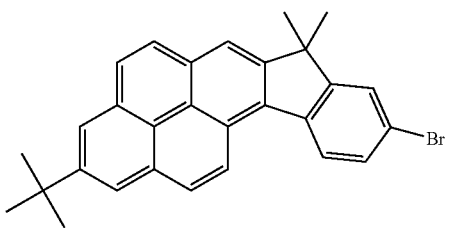

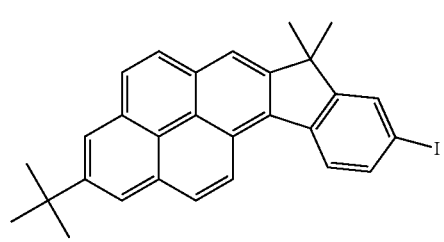

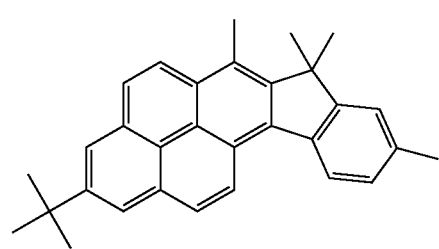

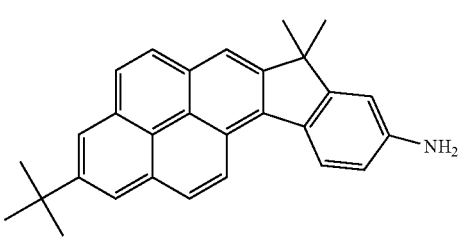

7
-continued

8
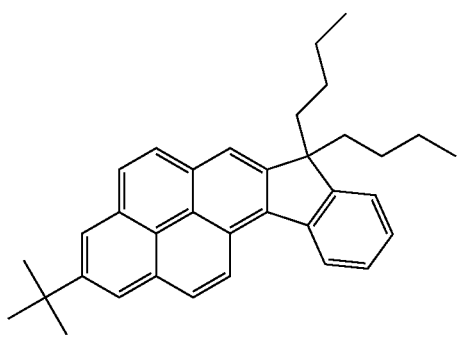

10
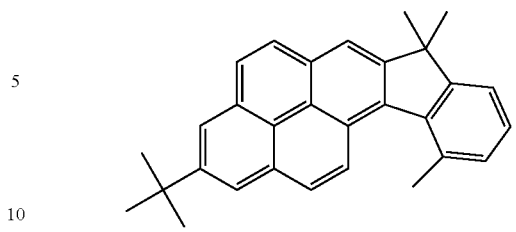

5

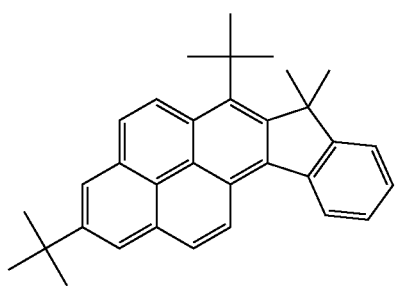

9

As a second preferred example of the first embodiment, a compound satisfying the following items (a) to (c) can be exemplified:

(a) $R^1$, $R^3$ to $R^5$, $R^9$, and $R^{11}$ to $R^{14}$ each represents a hydrogen atom; (b) $R^2$, $R^6$, $R^7$, and $R^8$ each independently represents a hydrogen atom or a substituted or unsubstituted alkyl group; and (c) $R^{10}$ represents a hydrogen atom, a substituted or unsubstituted aromatic group, or a substituted or unsubstituted fused polycyclic aromatic group.

Specific examples of the second preferred example are shown below. However, the present invention is not limited thereto.

11
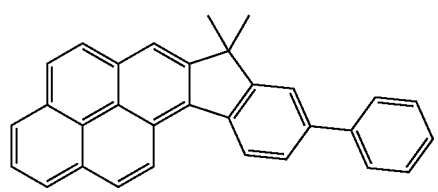

12
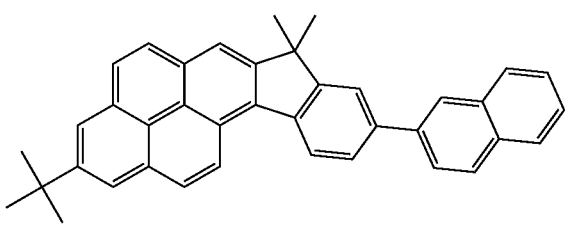

13
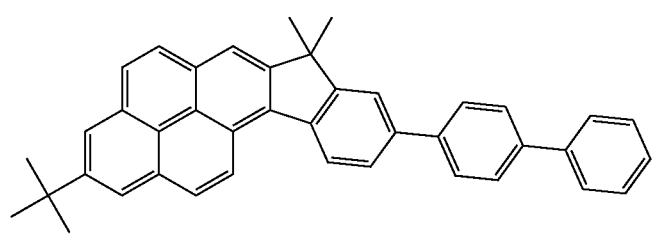

14
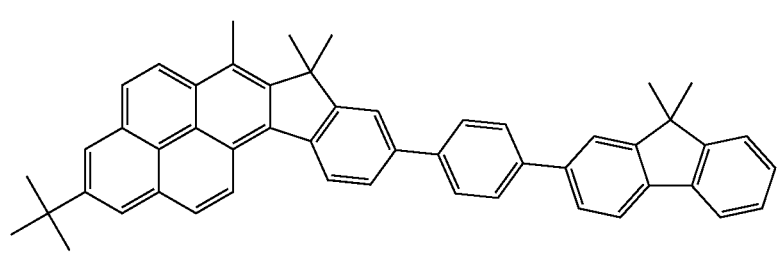

15
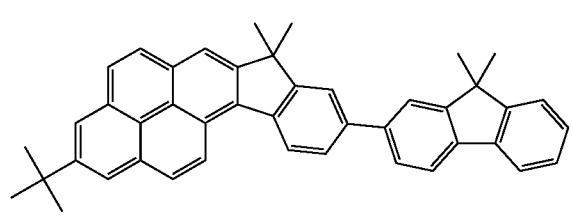

16
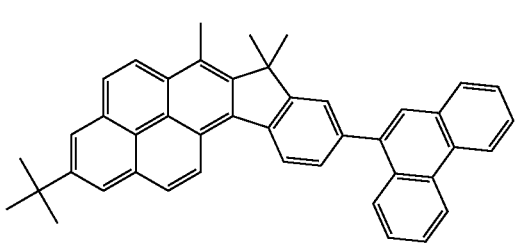

-continued
17
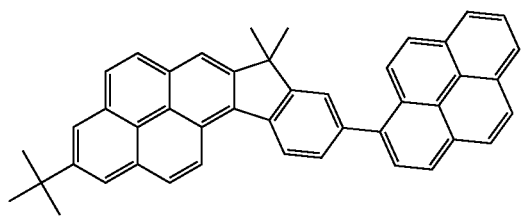
18
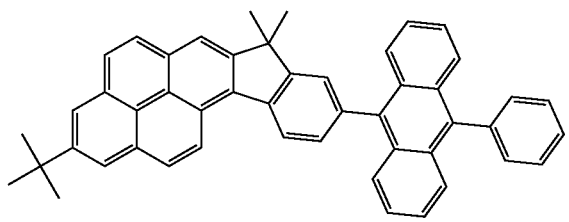
19
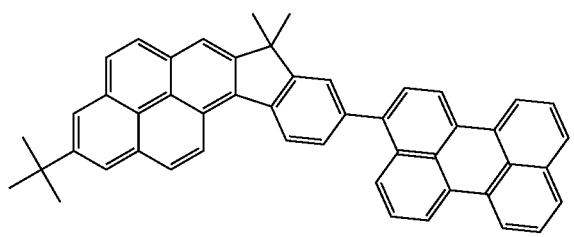
20
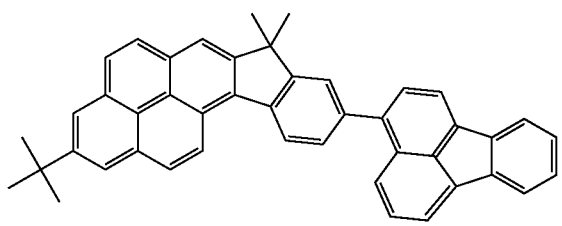
21
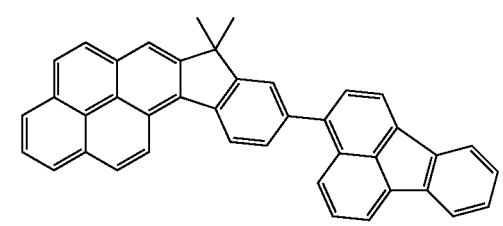
22
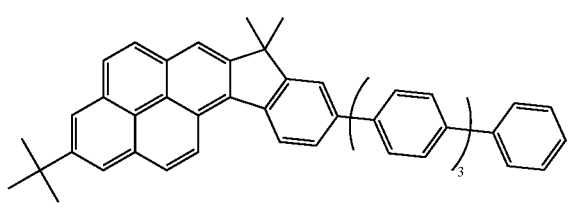
23
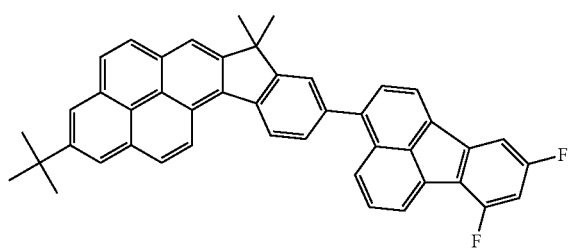
24
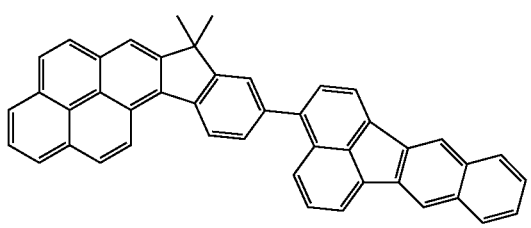
25
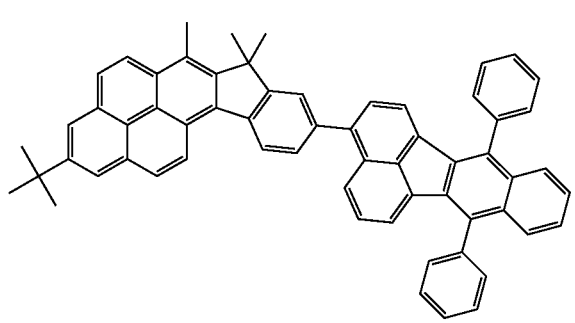
26
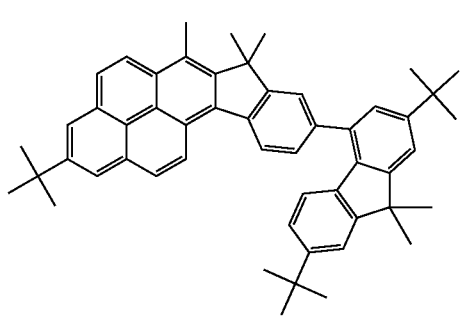
27
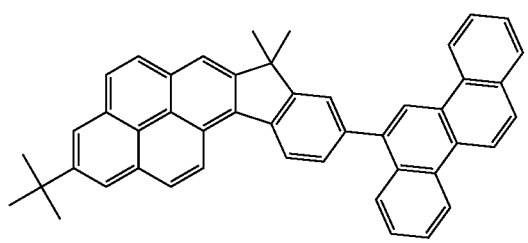
28
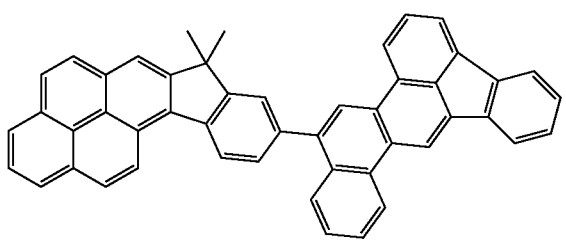

-continued

29

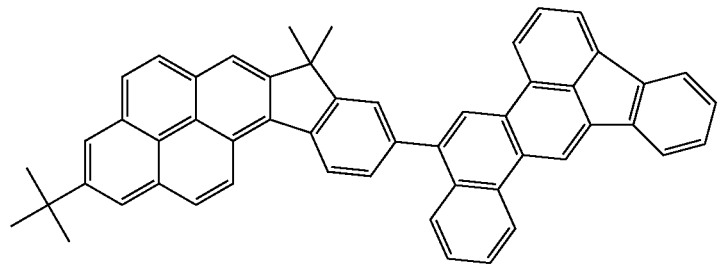

30

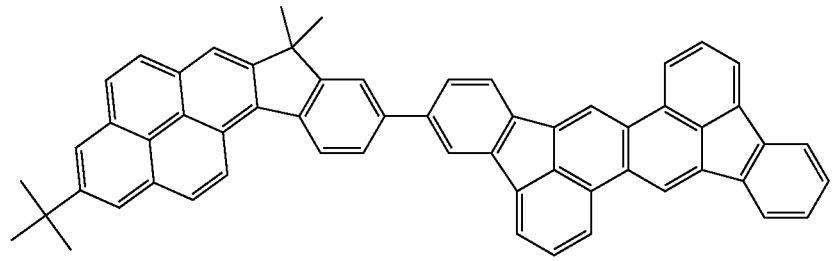

As a third preferred example of the first embodiment, a compound satisfying the following items (a) to (c) can be exemplified:
(a) $R^1$, $R^3$ to $R^6$, $R^9$, and $R^{11}$ to $R^{14}$ each represents a hydrogen atom; (b) $R^2$, $R^7$, and $R^8$ each independently represents a hydrogen atom or a substituted or unsubstituted alkyl group; and (c) $R^{10}$ represents a substituted or unsubstituted fused polycyclic aromatic group or a substituted or unsubstituted amino group.

Specific examples of the third preferred example are shown below. However, the present invention is not limited thereto.

31

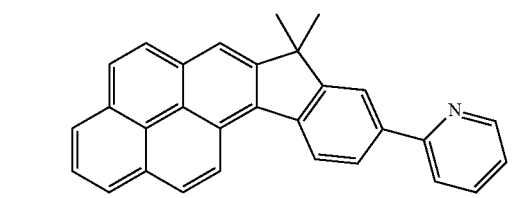

32

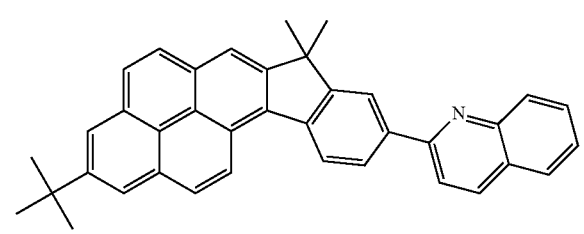

33

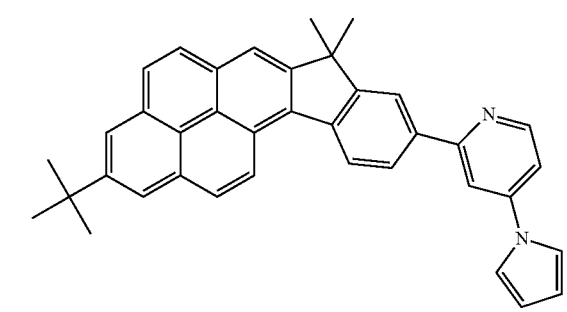

-continued

34

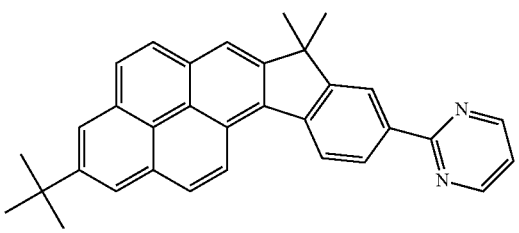

35

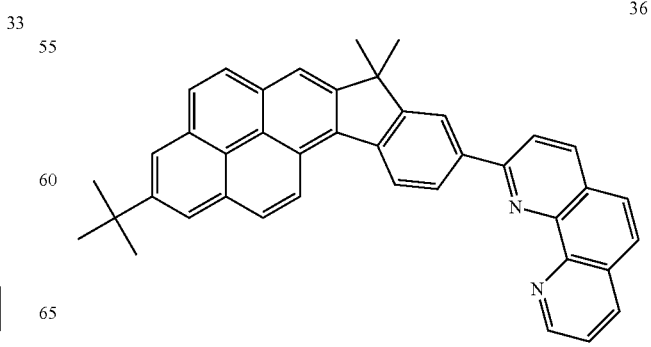

36

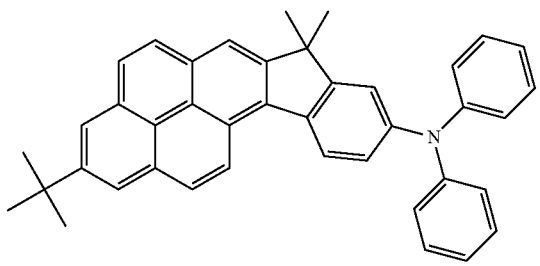

37

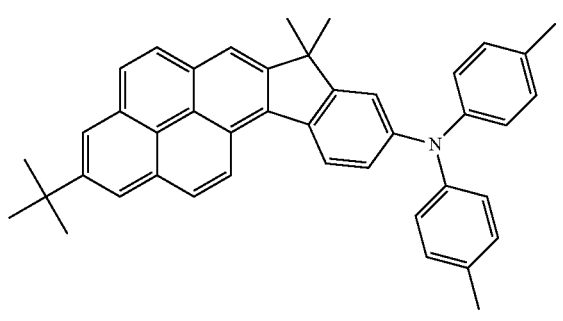

38

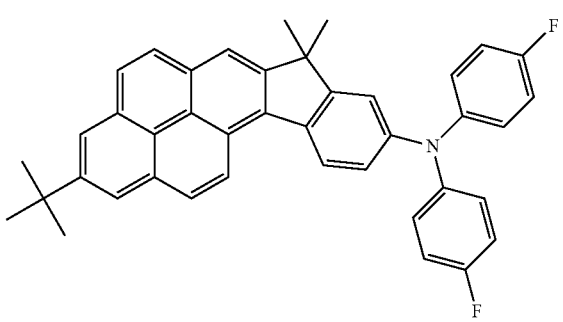

39

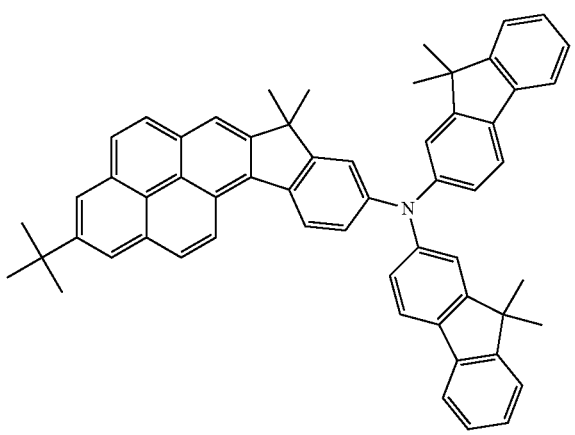

40

Next, the indenopyrene compound represented by the formula [2] (second embodiment) is described.

In the formula [2], n represents an integer of from 2 to 4.

In the formula [2], L represents: a single bond; a substituent selected from a substituted or unsubstituted alkylene group, a substituted or unsubstituted alkenylene group, and a substituted or unsubstituted alkynylene group; or a substituent selected from an n-valent substituted or unsubstituted aromatic group, an n-valent substituted or unsubstituted heterocyclic group, an n-valent substituted or unsubstituted fused polycyclic aromatic group, and an n-valent substituted or unsubstituted fused polycyclic heterocyclic group.

Examples of the alkylene group represented by L include, but are not limited to, an ethylene group, a propylene group, and a butylene group.

Examples of the alkenylene represented by L include, but are not limited to, a vinylene group, a propenylene group, and a butenylene group.

Examples of the alkynylene group represented by L include, but are not limited to, an ethynylene group, a propynylene group, a 1-methyl-2-propynylene group, a 1-ethyl-2-propynylene group, and a butynylene group.

Examples of the n-valent aromatic group represented by L include, but are not limited to, an n-valent substituent derived from benzene, biphenyl, or the like.

Examples of the n-valent heterocyclic group represented by L include, but are not limited to, an n-valent substituent derived from pyridine, biphenyl, or the like.

Examples of the n-valent fused polycyclic aromatic group represented by L include, but are not limited to, an n-valent substituent derived from fluorene, bifluorene, naphthalene, anthracene, chrysene, pyrene, or the like.

Examples of the n-valent fused polycyclic heterocyclic group represented by L include, but are not limited to, an n-valent substituent derived from azafluorene, diazafluorene, naphthylidine, or the like.

Examples of substituents which the alkylene group, alkenylene group, alkynylene group, n-valent aromatic group, n-valent heterocyclic group, n-valent fused polycyclic aromatic group, and n-valent fused polycyclic heterocyclic group may further have include, but are not limited to, alkyl groups such as a methyl group, an ethyl group, a propyl group, and a tert-butyl group, aromatic groups such as a phenyl group and a biphenyl group, heterocyclic groups such as a thienyl group and a pyrrolyl group, a cyano group, and a nitro group.

In the formula [2], $R^1$ to $R^9$ and $R^{11}$ to $R^{14}$ each independently represents a substituent selected from a hydrogen atom, a substituted or unsubstituted alkyl group, a substituted or unsubstituted alkenyl group, a substituted or unsubstituted alkynyl group, a substituted or unsubstituted aromatic group, a substituted or unsubstituted heterocyclic group, a substituted or unsubstituted fused polycyclic aromatic group, a substituted or unsubstituted fused polycyclic heterocyclic group, a halogen atom, and a substituted or unsubstituted amino group.

$R^1$, $R^3$ to $R^9$, and $R^{11}$ to $R^{14}$ in the formula [2] each preferably represents a hydrogen atom.

$R^2$, $R^6$, $R^7$, and $R^8$ in the formula [2] each preferably represents a hydrogen atom or a substituted or unsubstituted alkyl group.

In the formula [2], specific examples of the substituents represented by $R^1$ to $R^9$ and $R^{11}$ to $R^{14}$ are the same as the specific examples of the substituents of $R^1$ to $R^{14}$ in the formula [1]. Further, in the case where the substituents represented by $R^1$ to $R^9$ and $R^{11}$ to $R^{14}$ each represent an alkyl group, an alkenyl group, an alkynyl group, an aromatic group, a heterocyclic group, a fused polycyclic heterocyclic group, or a fused polycyclic aromatic group, they may further have a substituent. Specific examples thereof are the same as the specific examples of $R^1$ to $R^{14}$ in the formula [1].

In the formula [2], $R^1$ to $R^9$ and $R^{11}$ to $R^{14}$ may be identical to or different from each other. Further, in the formula [2], among the substituents which 2 to 4 indenopyrene skeletons each have, the substituents having the same numerals may be identical to or different from each other. That is, among the substituents $R^1$ to $R^9$ and $R^{11}$ to $R^{14}$ in the formula [2] which 2 to 4 indenopyrene skeletons have, the substituents having the same numerals may be identical to or different from each other.

Next, specific examples of the second embodiment are described below.

Specific examples of the second embodiment are shown below. However, the present invention is not limited thereto.

41

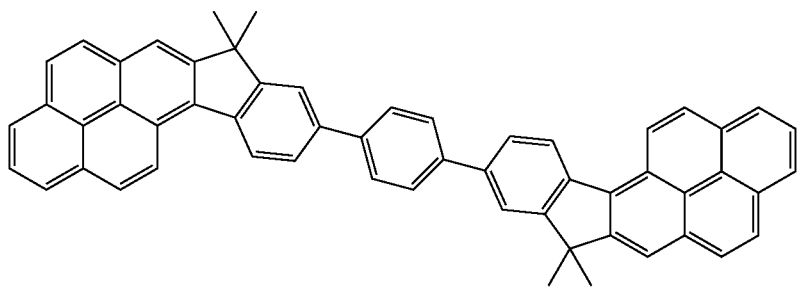

42

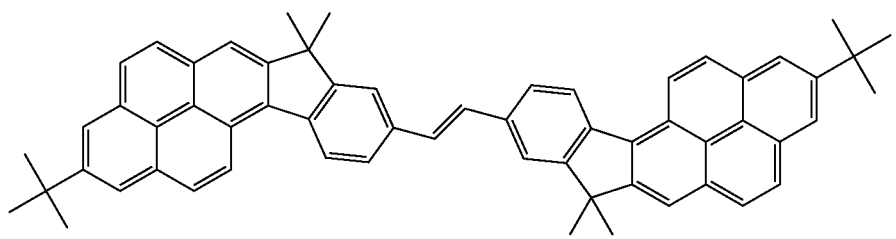

43

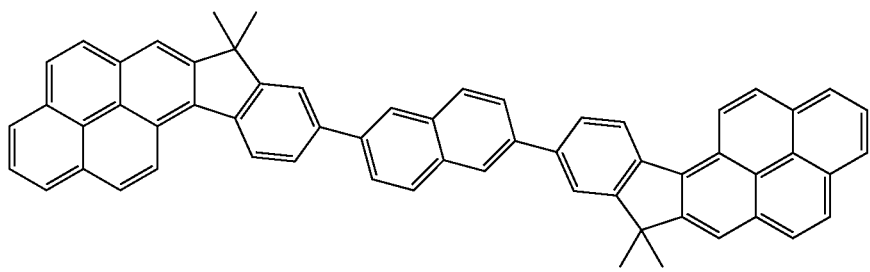

44

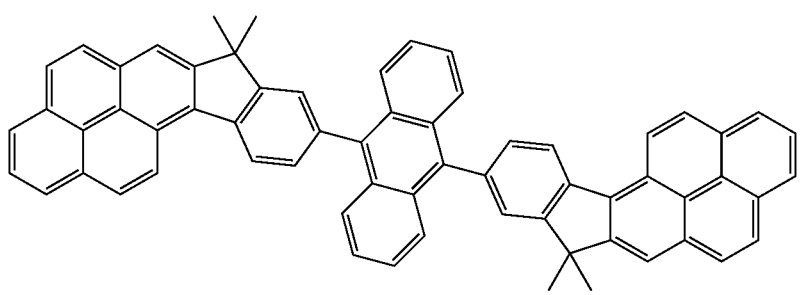

45

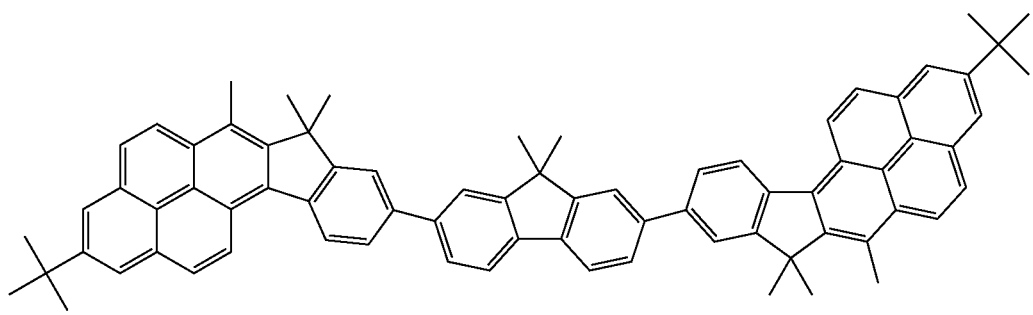

46
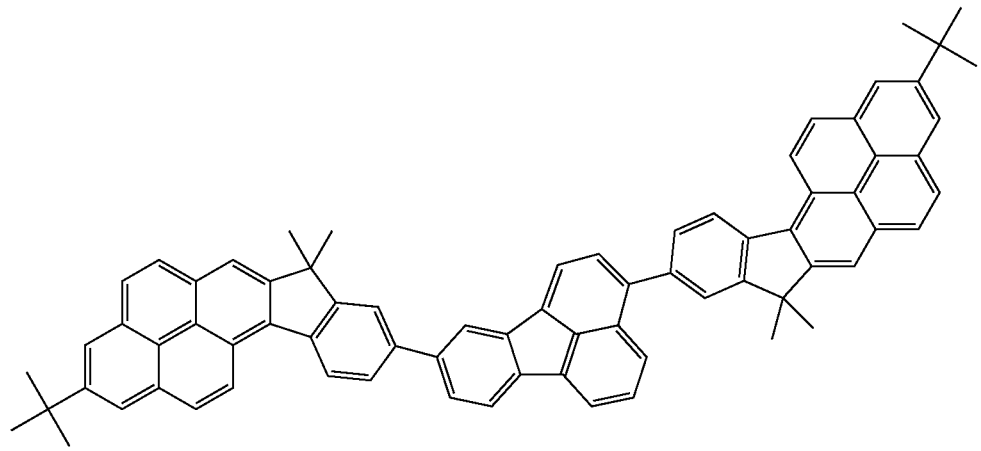
47
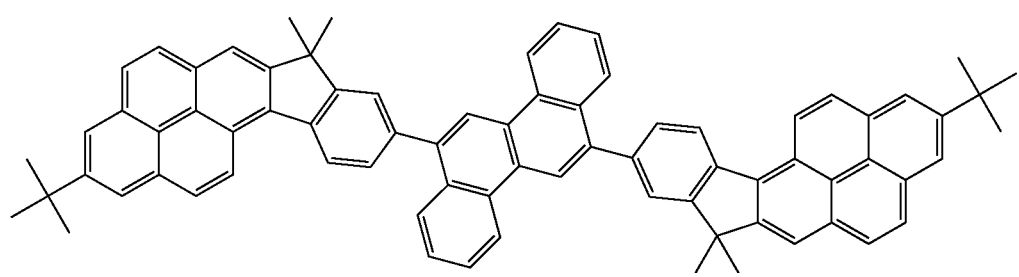
48
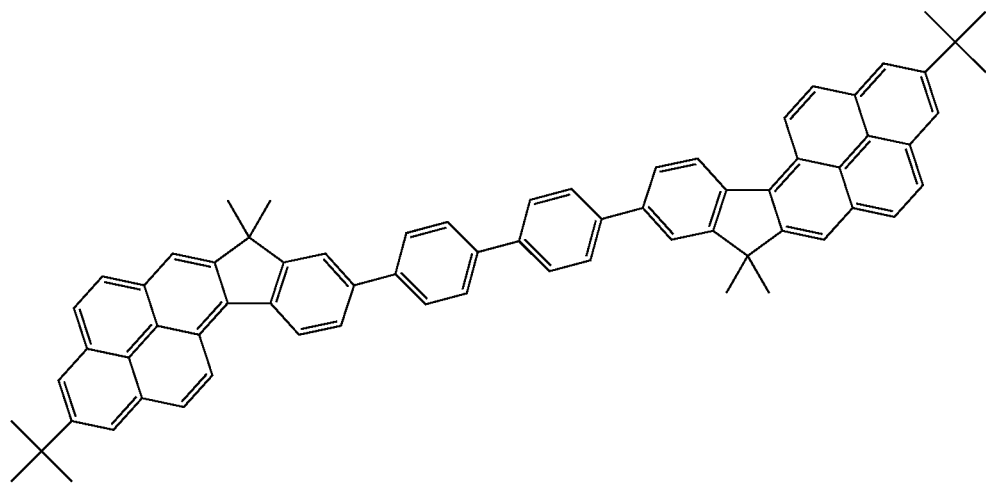

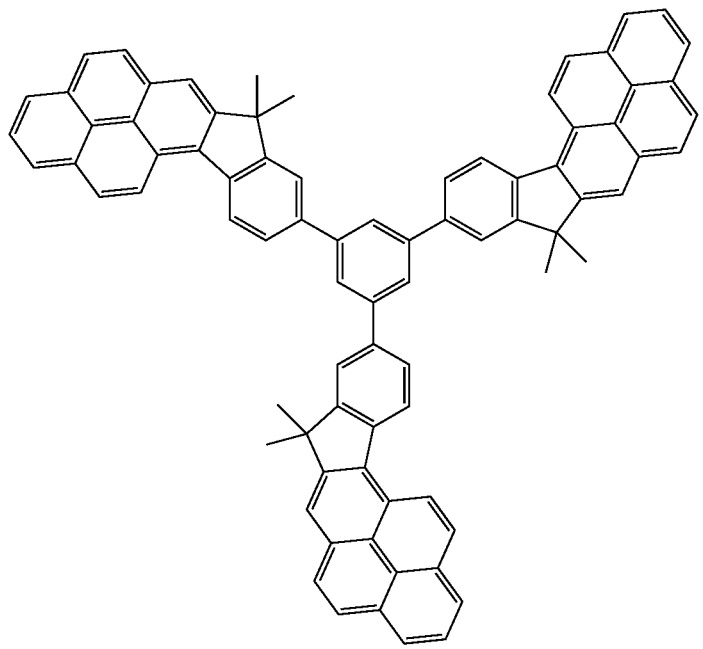

49

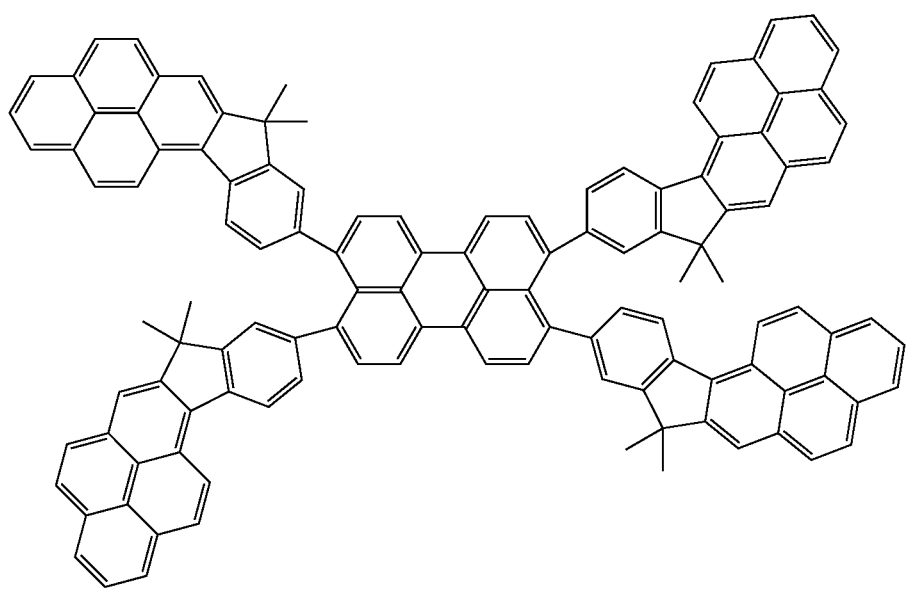

50

The indenopyrene compound of the present invention can be used as a constituent material of an organic light-emitting device, in particular, as a constituent material of a light-emitting layer. The organic light-emitting device in which the indenopyrene compound of the present invention is used as a constituent material of the light-emitting layer is excellent in color purity and light emitting efficiency.

Meanwhile, according to Steaven L. Murov, Ian Carmichael, Gordon L. Hug, Handbook of Photochemistry, 1993, pyrene has a quantum yield of 0.65 and fluorene has a quantum yield of 0.68, and hence, both pyrene and fluorene have high quantum yields. Therefore, this indicates that a compound in which pyrene and fluorene are bonded via a single bond or the like has a high quantum yield. In fact, there is disclosed an example that the light emitting efficiency and the like are improved in a compound in which a pyrene derivative and a fluorene derivative are bonded via a single bond or the like (refer to Japanese Patent Application Laid-Open No. 2005-325097, Japanese Patent Application Laid-Open No. 2006-151845, Japanese Patent Application Laid-Open No. 2007-63285, Japanese Patent Application Laid-Open No. 2007-145799, and Japanese Patent Application Laid-Open No. 2007-169182).

On the other hand, an indenopyrene compound containing, in one skeleton and not via a single bond or the like, a pyrene skeleton and a fluorene skeleton also has a high quantum yield. Further, an indenopyrene skeleton has a structure more rigid than a structure of a compound in which a pyrene skeleton and a fluorene skeleton are bonded via a single bond or the like. Therefore, the indenopyrene compound has a small Stokes shift and high oscillator strength in a specific transition, and hence, the color purity of the device is improved. It should be noted that examples of the indenopyrene compound include indeno[1,2-a]pyrene, indeno[2,1-a]pyrene, indeno[1, 2-e]pyrene, and indeno[2,1-e]pyrene. Of those compounds, indeno[1,2-a]pyrene has high oscillator strength and can be synthesized easily, and hence can be produced at low cost, from the result of a molecular orbital calculation.

Next, the organic light-emitting device of the present invention is described in detail.

The organic light-emitting device of the present invention comprises an organic layer between the anode and the cathode. Further, one of the anode and the cathode is a transparent electrode or a semi-transparent electrode.

The organic layer may be formed of one layer or multiple layers.

In a first specific example, an organic light-emitting device is formed of, in the following order, a substrate, an anode, a light-emitting layer, and a cathode.

In a second specific example, an organic light-emitting device is formed of, in the following order, a substrate, an anode, a hole-transporting layer, an electron-transporting layer, and a cathode. In this case, the hole-transporting layer and the electron-transporting layer function as a light-emitting layer.

In a third specific example, an organic light-emitting device is formed of, in the following order, a substrate, an anode, a hole-transporting layer, a light-emitting layer, an electron-transporting layer, and a cathode.

In a fourth specific example, an organic light-emitting device is formed of, in the following order, a substrate, an anode, a hole-injection layer, a hole-transporting layer, a light-emitting layer, an electron-transporting layer, and a cathode.

In a fifth specific example, an organic light-emitting device is formed of, in the following order, a substrate, an anode, a hole-transporting layer, a light-emitting layer, a hole/exciton blocking layer, an electron-transporting layer, and a cathode.

As shown in those examples, the organic layer placed between the anode and the cathode may be formed of various functional layers. Then, the indenopyrene compound of the present invention is contained in at least one layer of those functional layers.

More preferred is the fifth specific example.

It should be noted that, in each of the specific examples, an electron-injection layer may be provided between the electron-transporting layer and the cathode, and the indenopyrene compound of the present invention may be contained in the electron-transporting layer. Further, the indenopyrene compound of the present invention is preferably contained in the light-emitting layer, the electron-transporting layer, or the hole-transporting layer, and more preferably contained in the light-emitting layer. It should be noted that, in the case where the organic layer is formed of multiple functional layers, the indenopyrene compound of the present invention may be contained in one layer of the multiple functional layers or may be contained in multiple layers of the multiple functional layers. Further, one kind of the indenopyrene compound of the present invention or two or more kinds of indenopyrene compounds of the present invention may be contained in one layer.

Further, the light-emitting layer may be constituted by the indenopyrene compound of the present invention alone, however, it is preferably constituted by a host and a guest.

When a light-emitting layer is formed of a carrier transporting host and a guest, a main process for light-emission includes the following several steps of:

1. transporting an electron or a hole in the light-emitting layer;
2. generating an exciton of the host;
3. transferring excitation energy between host molecules; and
4. transfer of the excitation energy from the host to the guest.

Desired energy transfer in each step and light-emission occur in competition with various deactivation steps.

Here, it is preferable that the emission quantum yield of a light-emitting material be large in order that the luminous efficiency of an organic light-emitting device may be improved. On the other hand, in order to improve the color purity of the organic light-emitting device, it is preferable that the oscillator strength of a specific transition of the light-emitting material be high.

Thus, when the indenopyrene compound of the present invention is used especially as the host or the guest of the light-emitting layer, the color purity and emission efficiency of the organic light-emitting device are improved.

When the indenopyrene compound of the present invention is used as the host for a light-emitting layer, the content thereof is 20 to 99.9 wt % based on a total weight of a material forming a light-emitting layer.

When the indenopyrene compound of the present invention is used as a guest for a light-emitting layer, the concentration of the guest is 0.01 to 80 wt %, and preferably 1 to 40 wt % based on the concentration of the host. The guest may be uniformly contained throughout the layer formed of the host or may be contained in the layer with a concentration gradient existing. In addition, by partially incorporating the guest into a certain area, the layer formed of the host may have an area where no guest material is included.

Meanwhile, irrespective of whether the indenopyrene compound of the present invention is used as a host for the light-emitting layer or as a guest for the light-emitting layer, the energy gap of the host is preferably wider than that of the guest.

The organic light-emitting device of the present invention uses the indenopyrene compound of the present invention especially as a material forming the light-emitting layer. Moreover, in addition to the indenopyrene compound, a hole-transporting material, a light-emitting material, an electron-transporting material, or the like, which are low molecular or polymer material and are conventionally known, may be used together as required.

Those compounds are exemplified below.

A hole-injection transporting material preferably has excellent mobility to facilitate the injection of a hole from an anode and to transport the injected hole to a light-emitting layer. As low molecular and high molecular materials having hole-injecting and transporting abilities include, but are not limited to, a triarylamine compound, a phenylene diamine compound, a triazole compound, an oxadiazole compound, an imidazole compound, a pyrazoline compound, a pyrazolone compound, an oxazole compound, a fluorenone compound, a hydrazone compound, a stilbene compound, a phthalocyanine compound, a porphyrin compound, and poly (vinylcarbazole), poly(silylene), poly(thiophene), and other conductive polymers.

As light-emitting materials other than the indenopyrene compound of the present invention, the following compounds can be given. Specific examples of the compounds include, but are not limited to, polycyclic fused aromatic compounds (including naphthalene compounds, phenanthrene compounds, fluorene compounds, pyrene compounds, tetracene compounds, coronene compounds, chrysene compounds, perylene compounds, 9,10-diphenylanthracene compounds, and rubrene); quinacridone compounds; acridone compounds; coumarin compounds; pyran compounds; Nile red; pyrazine compounds; benzoimidazole compounds; benzothiazole compounds; benzoxazole compounds; stilbene compounds; organometallic complexes (including organic aluminum complexes such as tris(8-quinolinolato)aluminum, and organic beryllium complexes); and high-molecular compounds such as poly(phenylene vinylene) compounds, poly (fluorene) compounds, poly(phenylene) compounds, poly (thienylene vinylene) compounds, and poly(acetylene) compounds.

The electron-injection transporting material may be arbitrarily selected from compounds each of which facilitates the injection of an electron from a cathode and has a function of transporting the injected electron to a light-emitting layer. In addition, the material is selected in consideration of, for example, a balance with the carrier mobility of the hole-transporting material. The materials having electron-injection transporting abilities include, but are not limited to, oxadiazole compounds, oxazole compounds, triazole compounds, thiadiazole compounds, pyrazine compounds, triazole compounds, triazine compounds, perylene compounds, quinoline compounds, quinoxaline compounds, fluorenone compounds, anthrone compounds, phenanthroline compounds, and organometallic complexes.

Next, other members constituting the organic light emitting device of the present invention are described.

A constituting material of an anode desirably has as large a work function as possible. Examples of the anode material include a single metal such as gold, platinum, silver, copper, nickel, palladium, cobalt, selenium, vanadium, or tungsten. In addition, each of alloys thereof and metal oxides such as tin oxide, zinc oxide, indium oxide, indium tin oxide (ITO), and indium zinc oxide may be used. Further, a conductive polymer such as polyaniline, polypyrrole, polythiophene, or polyphenylene sulfide may also be used. Each of those electrode substances may be used alone, or two or more kinds of them may be used in combination. Further, the anode may be formed of a single layer or multiple layers.

Meanwhile, a constituting material of a cathode preferably has a small work function, and examples thereof include a single metal such as lithium, sodium, potassium, calcium, magnesium, aluminum, indium, ruthenium, titanium, manganese, yttrium, silver, lead, tin, or chromium. In addition, those metals may be combined to form alloys, such as a lithium-indium alloy, a sodium-potassium alloy, a magnesium-silver alloy, an aluminum-lithium alloy, an aluminum-magnesium alloy, or a magnesium-indium alloy, which may be used. A metal oxide such as indium tin oxide (ITO) may also be used. Each of those electrode materials may be used alone, or two or more kinds thereof may be used in combination. Further, the cathode may be formed of a single layer or multiple layers.

A substrate to be used in the organic light-emitting device of the present invention is, but not particularly limited to, an opaque substrate such as a metallic substrate or a ceramic substrate, or a transparent substrate of glass, quartz, a plastic sheet, or the like. In addition, colored light may be controlled by using a color filter film, a fluorescent color conversion filter film, a dielectric reflective film, or the like as the substrate.

It should be noted that the produced device may be provided with a protective layer or a sealing layer for the purpose of preventing the device from contacting with, for example, oxygen or moisture. Examples of the protective layer include: an inorganic material film such as a diamond thin film, a metal oxide, or a metal nitride; a polymer film such as a fluorine resin, polyparaxylene, polyethylene, a silicone resin, or a polystyrene resin; and further, a photocurable resin. In addition, the device itself may be covered with, for example, glass, a gas impermeable film, or a metal, and packaged with an appropriate sealing resin.

A thin film transistor (TFT) may be produced on a substrate, and then the device of the present invention may be produced to be connected to TFT.

Regarding the emission direction of a device, the device may have a bottom emission structure (structure in which light is emitted from a substrate side) or a top emission structure (structure in which light is emitted from an opposite side of the substrate).

In the organic light-emitting device of the present invention, the layer containing the indenopyrene compound of the present invention and the layers formed of other organic compounds are each formed by the following methods. The layer is generally formed by a vacuum deposition method, an ionized deposition method, sputtering, or plasma. In particular, a layer formed using a vacuum deposition method or a solution coating method is preferable because the layer hardly undergoes crystallization or the like, and is excellent in stability over time. Further, a thin film may be formed using a known coating method in which a compound is dissolved in an appropriate solvent (such as a spin coating, dipping, casting, LB, or inkjet method). In film formation by a coating method, in particular, a film may be formed by using a compound in combination with an appropriate binder resin.

The binder resin may be selected from a wide variety of binder resins. Examples of the binder resin include, but are not limited to, a polyvinyl carbazole resin, a polycarbonate resin, a polyester resin, a polyarylate resin, a polystyrene resin, an ABS resin, a polybutadine resin, a polyurethane resin, an acrylic resin, a methacrylic resin, a butyral resin, a polyvinyl acetal resin, a polyamide resin, a polyimide resin, a polyethylene resin, a polyethersulfone resin, a diallyl phthalate resin, a phenol resin, an epoxy resin, a silicone resin, a polysulfone resin, and a urea resin. Each of those resins may be used alone, or one kind or two or more kinds of them may be mixed as a copolymer. Further, an additive such as a known plasticizer, antioxidant, or ultraviolet absorber may be used together if required.

EXAMPLES

Hereinafter, the present invention is described specifically by way of examples; provided that the present invention is not limited to those examples.

Example 1

Production Method of Exemplified Compound 3

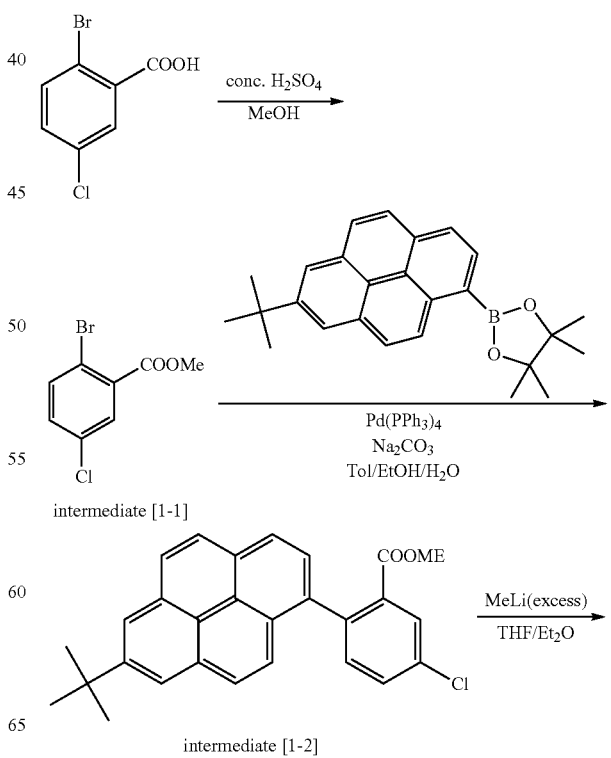

-continued

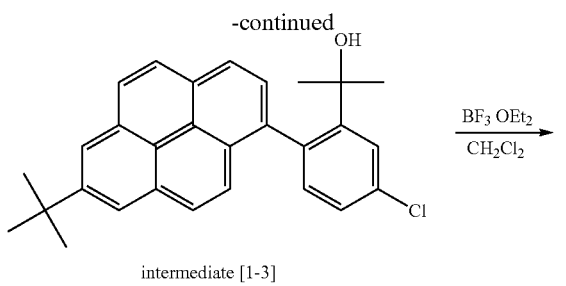

intermediate [1-3]

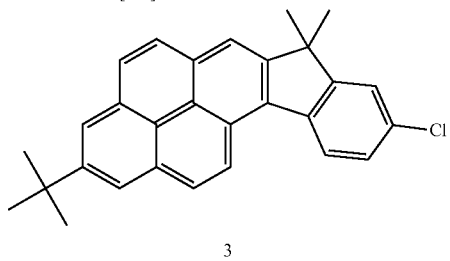

3

Intermediate (1) Synthesis of Intermediate [1-1] (methyl 2-bromo-5-chlorobenzoate)

With reference to a synthesis method described in Journal of Organic Chemistry 2003, 68, 11, 4588, 2-bromo-5-chlorobenzoic acid was used as a starting material and Intermediate [1-1] (methyl 2-bromo-5-chlorobenzoate) was synthesized.

(2) Synthesis of Intermediate [1-2] (methyl 2-(7-tert-butylpyrene-1-yl)-5-chlorobenzoate)

With reference to a synthesis method described in Synthetic Metals, 143(1), 89-96, 2004, Intermediate [1-1] (methyl 2-bromo-5-chlorobenzoate) was used as a starting material and Intermediate [1-2] (methyl 2-(7-tert-butylpyrene-1-yl)-5-chlorobenzoate) was synthesized.

(3) Synthesis of Intermediate [1-3] (2-(2-(7-tert-butylpyrene-1-yl)-5-chlorophenyl)propane-2-ol)

Intermediate [1-2] (methyl 2-(7-tert-butylpyrene-1-yl)-5-chlorobenzoate) was used as a starting material and Intermediate [1-3] (2-(2-(7-tert-butylpyrene-1-yl)-5-chlorophenyl) propane-2-ol) was obtained. The synthesis was performed with reference to a synthesis method described in Journal of Organic Chemistry 2000, 65, 21, 6982.

(4) Synthesis of Exemplified Compound 3

Under a nitrogen atmosphere, the following reagent and solvent were put in a round bottom flask.
Intermediate [1-3]: 3.710 g
Dichloromethane: 100 mL
Next, the reaction mixture was cooled to 5° C., and then the following reagent was added.
Boron fluoride etherate: 0.2 mL
Next, the reaction mixture was stirred for 15 minutes at room temperature. After that, 10 mL of methanol was added to the reaction mixture to quench the reaction. Then, an organic phase was washed with water twice. After that, the solvent was removed by distillation under reduced pressure. Next, the resultant product was washed with heptane and methanol to obtain 1.324 g of Exemplified Compound 3 as a yellow powder.

Matrix-assisted laser desorption/ionization time-of-flight mass spectrometry (MALDI-TOF MS) confirmed that the compound had an M+ of 408.5.

The structure of Exemplified Compound 3 was identified by NMR measurement. The assignment of a peak is shown below.

$^1$H-NMR (CDCl$_3$): δ (ppm)=8.87 (1H, d, J=9.16 Hz), 8.42 (1H, d, J=8.47 Hz), 8.25 (2H, d, J=1.98 Hz), 8.22 (1H, d, J=9.39 Hz), 8.18 (1H, s), 8.07 (2H, d, J=1.37 Hz), 7.56 (1H, d, J=2.06 Hz), 7.48 (1H, dd, J1=8.47, J2=2.06 Hz).

PL spectrum of Exemplified Compound 3 in a toluene solution was measured. As a result, a PL spectrum shown in FIG. 1 was obtained. The PL spectrum was a blue emission spectrum having an emission peak at 423 nm and a half width of 36 nm.

Exemplified Compound 3 was evaluated for its quantum yield by the following method.

First, a toluene solution having a concentration of approximately $10^{-7}$ mol/l was prepared, and the absorbance of the solution at a wavelength of 350 nm was measured with a spectrophotometer (U-3310 manufactured by Hitachi, Ltd.). Next, the emission spectrum of the solution when a wavelength of 350 nm was defined as an excitation wavelength was measured with a fluorophotometer (F-4500 manufactured by Hitachi, Ltd.). A relative value for the emission quantum yield of the compound when a value for diphenylanthracene was assumed to be 0.95 was determined from the peak area of the emission spectrum and the absorbance. Table 1 shows the result.

Further, exemplified compounds to be described below can be synthesized by changing the material used in Example 1 as follows.

(Exemplified Compound 1)
2-pyrenyl-4,4,5,5-tetramethyl-1,3,2-dioxaborolane is used instead of 2-(7-tert-butylpyrene-1-yl)-4,4,5,5-tetramethyl-1,3,2-dioxaborolane. Further, 2-bromobenzoic acid is used instead of 2-bromo-5-chlorobenzoic acid. Thus, Exemplified Compound 1 can be synthesized.

(Exemplified Compound 2)
2-(7-tert-butyl-3-methylpyrene-1-yl)-4,4,5,5-tetramethyl-1,3,2-dioxaborolane is used instead of 2-(7-tert-butylpyrene-1-yl)-4,4,5,5-tetramethyl-1,3,2-dioxaborolane. Thus, Exemplified Compound 2 can be synthesized.

(Exemplified Compound 6)
2-(7-tert-butyl-3-methylpyre-1-nyl)-4,4,5,5-tetramethyl-1,3,2-dioxaborolane is used instead of 2-(7-tert-butylpyrene-1-yl)-4,4,5,5-tetramethyl-1,3,2-dioxaborolane. Further, 2-bromo-5-methylbenzoic acid is used instead of 2-bromo-5-chlorobenzoic acid. Thus, Exemplified Compound 6 can be synthesized.

(Exemplified Compound 7)
2-bromo-5-aminobenzoic acid is used instead of 2-bromo-5-chlorobenzoic acid. Thus, Exemplified Compound 7 can be synthesized.

(Exemplified Compound 10)

2-bromo-3-methylbenzoic acid is used instead of 2-bromo-5-chlorobenzoic acid. Thus, Exemplified Compound 10 can be synthesized.

Example 2

Production method of Exemplified Compound 26

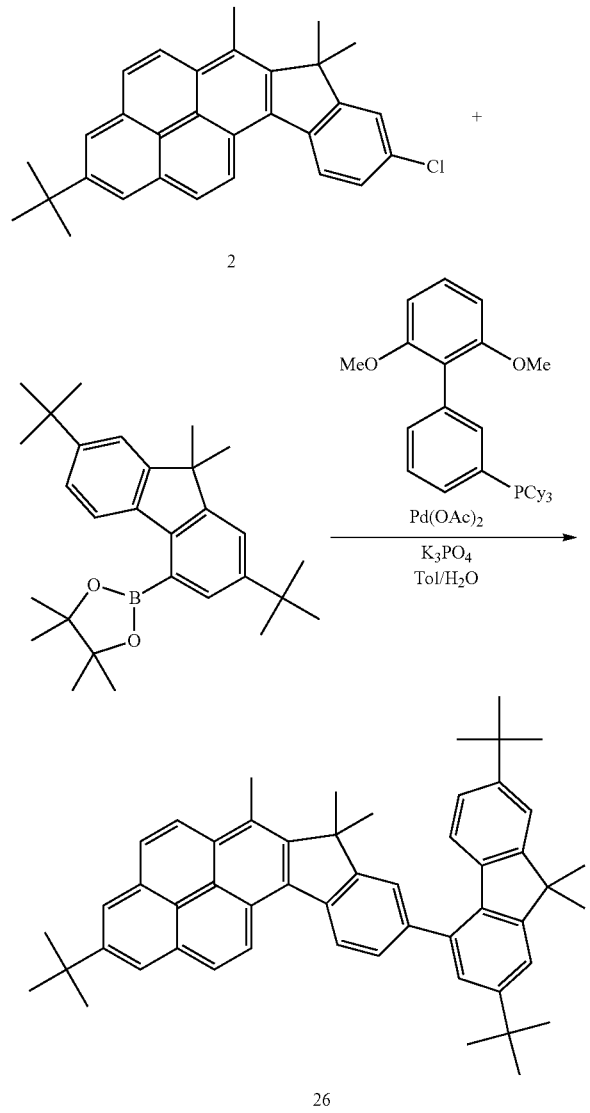

(1) Synthesis of Exemplified Compound 26

Under a nitrogen atmosphere, the following reagent and solvent were put in a round bottom flask.

Exemplified Compound 2: 119 mg
2-(2,7-di-tert-butyl-9,9-dimethyl-9H-fluoren-4-yl-)4,4,5,5-tetramethyl-1,3,2-dioxaborolane: 144 mg (0.33 mmol)
Palladium acetate: 15 mg
Dicyclohexyl(2',6'-dimethoxybiphenyl-2-yl)phosphine: 48 mg
Potassium phosphate: 357 mg
Toluene: 80 mL
Water: 10 mL Next, the reaction mixture was stirred for 3 hours while being refluxed under heat. After that, the reaction mixture was cooled to room temperature, and water was added to quench the reaction. Then an organic phase was separated and then washed with brine thrice and with water once. After that, the solvent was removed by distillation under reduced pressure to obtain a crude product. Next, the crude product was purified by silica gel chromatography (toluene/heptane, ratio 1/4), whereby 118 mg of Exemplified Compound 26 were obtained.

Matrix-assisted laser desorption/ionization time-of-flight mass spectrometry (MALDI-TOF MS) confirmed that the compound had an M+ of 692.4.

The structure of the compound was identified by NMR measurement. The assignment of a peak is shown below.

$^1$H-NMR (CDCl$_3$): δ (ppm)=9.07 (1H, d, J=9.39 Hz), 8.65 (1H, d, J=8.01 Hz), 8.37 (1H, d, J=9.16 Hz), 8.23 (2H, s), 8.17 (1H, d, J=9.16 Hz), 8.12 (1H, d, J=9.16 Hz), 7.78 (1H, d, J=1.60 Hz), 7.64 (1H, d, J=7.79 Hz), 7.48 (1H, d, J=1.83 Hz), 7.43 (1H, d, J=1.60 Hz), 7.33 (1H, d, J=1.83 Hz), 7.09 (1H, d, J=8.24 Hz), 7.03-7.00 (1H, M), 3.20 (3H, s), 1.61 (9H, s), 1.517 (3H, s), 1.514 (6H, s), 1.511 (3H, s), 1.45 (9H, s), 1.30 (9H, s).

Figure 2:
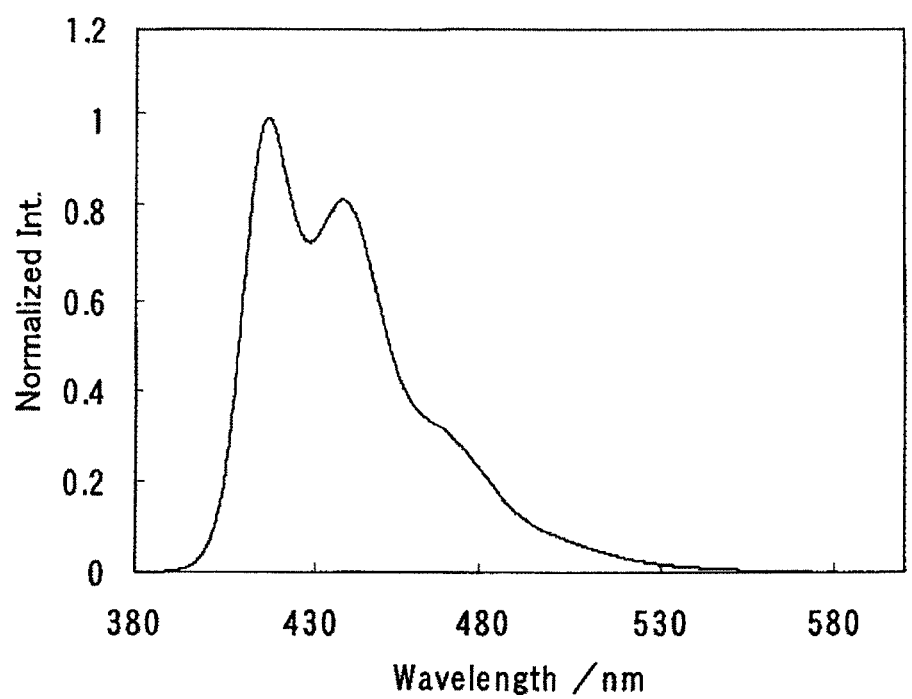
FIG. 2 is a view illustrating the PL spectrum of a toluene solution of Exemplified Compound 26.

A PL spectrum of Exemplified Compound 26 in a toluene solution was measured. As a result, a PL spectrum shown in FIG. 2 was obtained. The PL spectrum was a blue emission spectrum having an emission peak at 417 nm and a half width of 43 nm.

The quantum yield of Exemplified Compound 26 was evaluated in the same manner as in Example 1. Table 1 shows the result.

Further, the following exemplified compounds can be synthesized by changing the materials used in Example 2 as follows.

(Exemplified Compound 13)

Exemplified Compound 3 is used instead of Exemplified Compound 2. Further, 2-[biphenyl-4-yl]-4,4,5,5-tetramethyl-1,3,2-dioxaborolane is used instead of 2-[2,7-di-tert-butyl-9,9-dimethyl-9H-fluoren-4-yl]-4,4,5,5-tetramethyl-1,3,2-dioxaborolane. Thus, Exemplified Compound 13 can be synthesized.

(Exemplified Compound 14)

2-[4-[9,9-dimethyl-9H-fluoren-2-yl]phenyl]-4,4,5,5-tetramethyl-1,3,2-dioxaborolane is used instead of 2-[2,7-di-tert-butyl-9,9-dimethyl-9H-fluoren-4-yl]-4,4,5,5-tetramethyl-1,3,2-dioxaborolane. Thus, Exemplified Compound 14 can be synthesized.

(Exemplified Compound 17)

Exemplified Compound 3 is used instead of Exemplified Compound 2. Further, 2-[pyren-1-yl]-4,4,5,5-tetramethyl-1,3,2-dioxaborolane is used instead of 2-[2,7-di-tert-butyl-9,9-dimethyl-9H-fluoren-4-yl]-4,4,5,5-tetramethyl-1,3,2-dioxaborolane. Thus, Exemplified Compound 17 can be synthesized.

(Exemplified Compound 27)

Exemplified Compound 3 is used instead of Exemplified Compound 2. 2-[chrysen-6-yl]-4,4,5,5-tetramethyl-1,3,2-dioxaborolane is used instead of 2-[2,7-di-tert-butyl-9,9-dimethyl-9H-fluoren-4-yl]-4,4,5,5-tetramethyl-1,3,2-dioxaborolane. Thus, Exemplified Compound 27 can be synthesized.

(Exemplified Compound 32)

Exemplified Compound 3 is used instead of Exemplified Compound 2. 2-[4,4,5,5-tetramethyl-1,3,2-dioxaborolan-2-yl]quinoline is used instead of 2-[2,7-di-tert-butyl-9,9-dimethyl-9H-fluoren-4-yl]-4,4,5,5-tetramethyl-1,3,2-dioxaborolane. Thus, Exemplified Compound 32 can be synthesized.

Example 3

Production method of Exemplified Compound 48

Intermediate

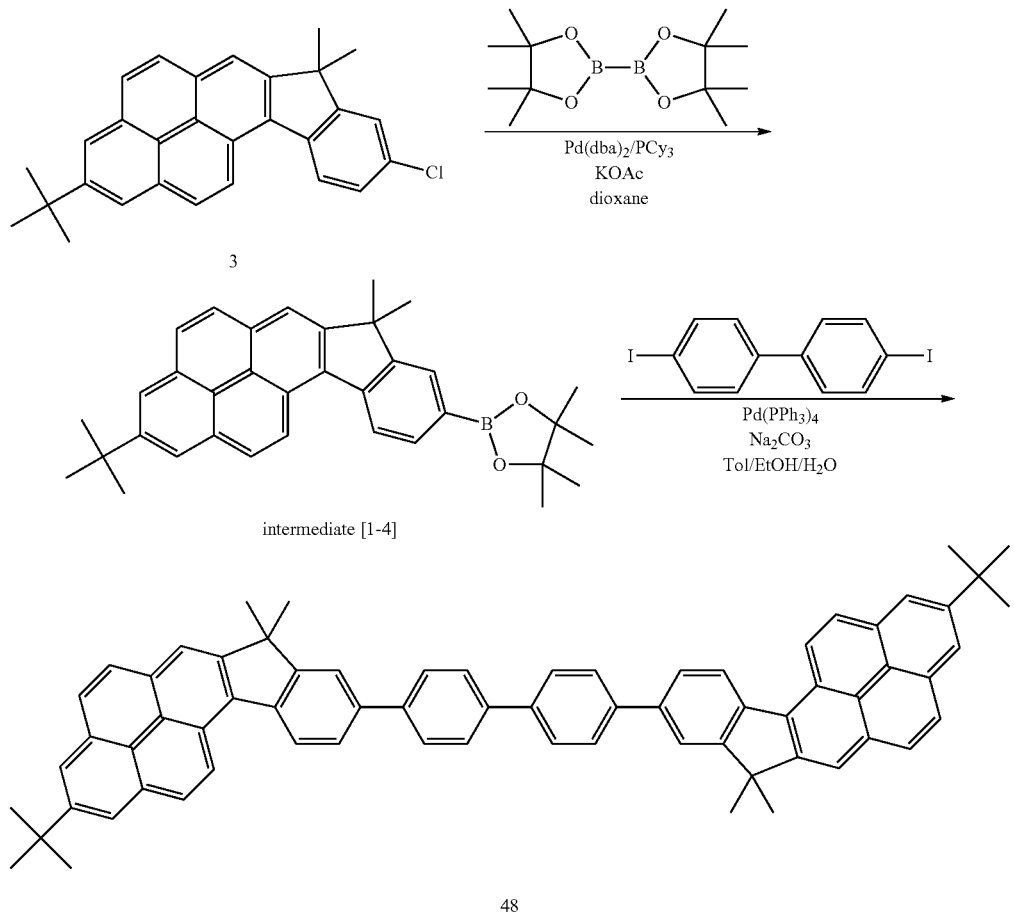

intermediate [1-4]

48

(1) Synthesis of Intermediate [1-4] (2-(2-tert-butyl-7,7-dimethyl-7H-indeno[1,2-a]pyrene-9-yl)-4,4,5,5-tetramethyl-1,3,2-dioxaborolane)

Exemplified Compound 3 was used as a starting material and Intermediate [1-4] (2-(2-tert-butyl-7,7-dimethyl-7H-indeno[1,2-a]pyrene-9-yl]- 4,4,5,5-tetramethyl-1,3,2-dioxaborolane) was synthesized. The synthesis was performed with reference to a method described in Tetrahedron 2001, 57, 9813.

(2) Synthesis of Exemplified Compound 48 under a nitrogen atmosphere, the following reagents and solvents were put in a round bottom flask.
Intermediate [1-5]: 1,300 g
4,4'-diiodobiphenyl: 380 mg
Tetrakistriphenylphosphin palladium: 50 mg
Sodium carbonate: 500 mg
Toluene: 40 mL
Ethanol: 10 mL
Water: 25 mL Next, the reaction mixture was stirred for 8 hours while being heated to reflux. Subsequently, the reaction mixture was cooled to room temperature, and after that, methanol was added thereto and washing and suction filtration were performed, to thereby obtain a crude crystal. Next, to the crude crystal was added chlorobenzene and the mixture was heated for dissolution at 120° C. After that, the resultant was purified by silica gel column chromatography. Next, the solvent was distilled off under reduced pressure to obtain a residue. The residue was then recrystallized with toluene, to thereby obtain 200 mg of Exemplified Compound 48 as a yellow powder.

Matrix-assisted laser desorption/ionization time-of-flight mass spectrometry (MALDI-TOF MS) confirmed that the compound had an M+ of 898.6.

The structure of the compound was identified by NMR measurement. The assignment of a peak is shown below.

$^1$H-NMR (ODB): δ (ppm)=8.27 (4H, s), 8.24 (4H, s), 8.23 (2H, s), 8.04 (4H, d, J=5.95 Hz), 7.98 (2H, s), 7.90 (4H, d, J=8.01 Hz), 7.83 (4H, d, J=8.47 Hz), 7.19 (4H, d, J=6.64 Hz), 1.77 (12H, s), 1.58 (18H, s).

Figure 3:
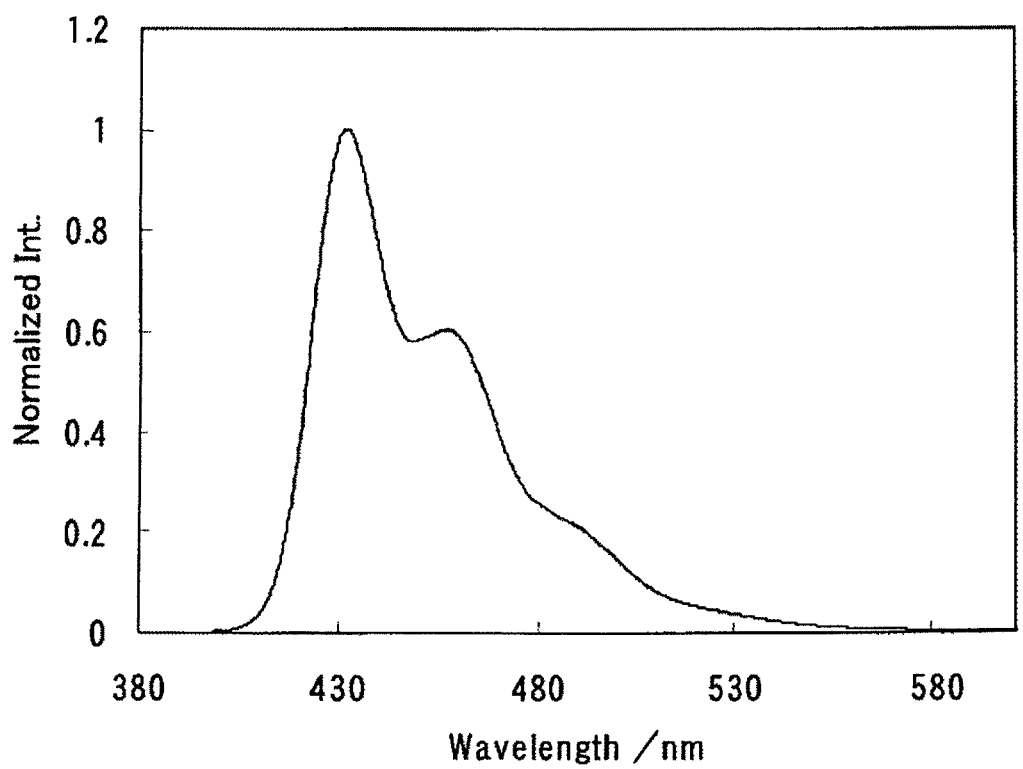
FIG. 3 is a view illustrating the PL spectrum of a toluene solution of Exemplified Compound 48.

A PL spectrum of Exemplified Compound 48 in a toluene solution was measured. As a result, a PL spectrum shown in FIG. 3 was obtained. The PL spectrum was a blue emission spectrum having an emission peak at 431 nm and a half width of 43 nm.

Exemplified Compound 48 was evaluated for its quantum yield by the same method as Example 1. Table 1 shows the results.

In addition, the following exemplified compounds can each be synthesized in the same manner as in Example 3 except that the following compounds are each used instead of 4,4'-diiodobiphenyl in Example 3.

(Exemplified Compound 42)

Exemplified Compound 42 can be synthesized by using [E]-1,2-diiodoethylene.

(Exemplified Compound 46)

Exemplified Compound 46 can be synthesized by using 3,8-dibromofluoranthene.

(Exemplified Compound 47)

Exemplified Compound 47 can be synthesized by using 6,12-dibromochrysene.

Comparative Example 1

With regard to pyrene (Compound A-0) shown below, first, a toluene solution having a concentration of approximately $10^{-7}$ mol/l was prepared, and the absorbance of the solution was measured at a wavelength of 332 nm by using a spectrophotometer (U-3310, manufactured by Hitachi, Ltd.). Next, the emission spectrum of the solution was measured when a wavelength of 332 nm was used as excitation wavelength by using a fluorescence spectrophotometer (F-4500, manufactured by Hitachi, Ltd.). The relative value of an emission quantum yield was determined from the peak area of the emission spectrum and the absorbance. Here, the emission quantum yield of Exemplified Compound 3 in Example 1 was assumed to be 0.55. Table 1 shows the result.

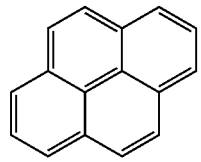

compound A0

TABLE 1

| Sample | | Relative quantum yield |
| --- | --- | --- |
| Example 1 | Exemplified Compound 3 | 0.55 |
| Example 2 | Exemplified Compound 26 | 0.69 |
| Example 3 | Exemplified Compound 48 | 0.77 |
| Comparative Example 1 | Compound A0 | 0.35 |

From Table 1, it was shown that the indenopyrene skeleton (Exemplified Compound 3) contained in the indenopyrene compound of the present invention had higher quantum yield compared with the pyrene skeleton (Compound A0). Consequently, it can be said that the indenopyrene skeleton itself which is contained in the indenopyrene compound of the present invention is a skeleton having a high quantum yield.

Further, it was found that a quantum yield could be further increased by a combined use with an appropriate substituent, as shown in the case of Exemplified Compound 48. Consequently, the luminance and the light emitting efficiency of an organic light-emitting device can be improved by using the indenopyrene compound of the present invention as a constituent material of the organic light-emitting device.

Example 4

An organic light-emitting device was produced by the following method.

Indium tin oxide (ITO) was formed into a film on a glass substrate (substrate) by a sputtering method so as to serve as the anode. At this time, the thickness of the anode was 120 nm. Next, the glass substrate on which the ITO film had been formed was subjected to ultrasonic cleaning with acetone and isopropyl alcohol (IPA) in the stated order. Next, the substrate was washed with pure water, and was then dried. Further, the substrate was subjected to UV/ozone cleaning. The substrate thus treated was used as a transparent conductive supporting substrate.

Next, Compound A1 represented below which is a hole-transporting material was mixed with chloroform, thereby preparing a chloroform solution at a concentration of 0.1 wt %.

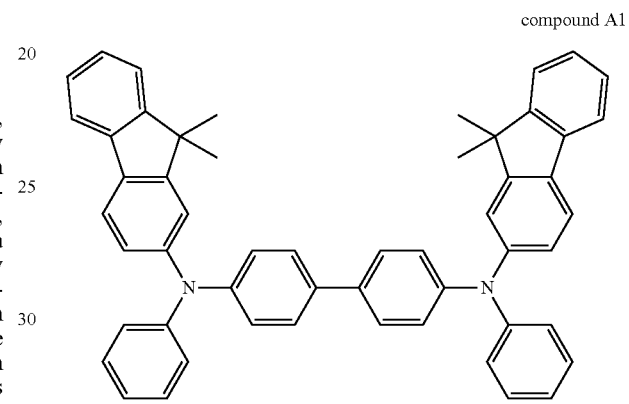

compound A1

Next, the solution was dropped onto the ITO electrode (anode), was subjected to spin coating by being rotated initially at a revolution of 500 RPM for 10 seconds, and then at a revolution of 1,000 RPM for 40 seconds, whereby a film was formed. After that, the thin film was dried in a vacuum oven at 80° C. for 10 minutes so that the solvent in the thin film might be completely removed. As a result, the hole-injection layer was formed. At this time, the thickness of the hole-injection layer was 15 nm.

Next, Compound A2 represented below was formed into a film as a hole-transporting layer on the hole-injection layer by a vacuum deposition method. At this time the thickness of the hole-transporting layer was 15 nm, the degree of vacuum at the time of the deposition was $1.0 \times 10^{-4}$ Pa, and the film formation rate was from 0.1 nm/sec to 0.2 nm/sec.

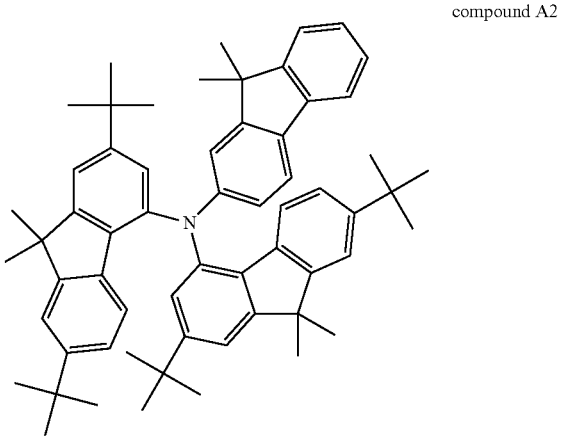 [SMILES: CC(C)(C)c1ccc2c(c1)C(C)(C)c1cc(C(C)(C)C)cc(N(c3ccc4c(c3)C(C)(C)c3ccccc3-4)c3cc(C(C)(C)C)cc4c3-c3ccc(C(C)(C)C)cc3C4(C)C)c1-2]

compound A2

Next, Compound A3 represented below as a host and Exemplified Compound 48 as a guest were co-deposited at a weight ratio of 99:1 from the vapor onto the hole-transporting layer by a vacuum deposition method, to thereby form a light-emitting layer. At this time, the light-emitting layer had a thickness of 30 nm, the degree of vacuum at the time of the deposition was $1.0 \times 10^{-4}$ Pa, and the film formation rate was from 0.1 nm/sec to 0.2 nm/sec.

compound A3

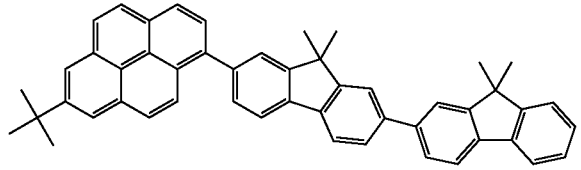

Next, 2,9-bis[2-(9,9'-dimethylfluorenyl)]-1,10-phenanthroline was formed into a film as an electron-transporting layer by a vacuum deposition method. At this time, the electron-transporting layer had a thickness of 30 nm, the degree of vacuum at the time of the deposition was $1.0 \times 10^{-4}$ Pa, and the film formation rate was from 0.1 nm/sec or more to 0.2 nm/sec or less.

Next, lithium fluoride (LiF) was formed into a film on the electron-transporting layer by a vacuum deposition method, to thereby form a LiF film. At this time, the LiF film had a thickness of 0.5 nm, the degree of vacuum at the time of the deposition was $1.0 \times 10^{-4}$ Pa, and the film formation rate was 0.01 nm/sec. Next, aluminum was formed into a film on the LiF film by a vacuum deposition method, to thereby form an aluminum film. At this time, the aluminum film had a thickness of 120 nm, the degree of vacuum at the time of the deposition was $1.0 \times 10^{-4}$ Pa, and the film formation rate was from 0.5 nm/sec and 1.0 nm/sec. Here, the lithium fluoride film and the aluminum film function as an electron-injection electrode (cathode).

Next, the resultant structure was covered with a protective glass plate in a dry air atmosphere lest the device should degrade owing to the adsorption of moisture, and was sealed with an acrylic resin-based adhesive. The organic light-emitting device was thus obtained.

Figure 4:
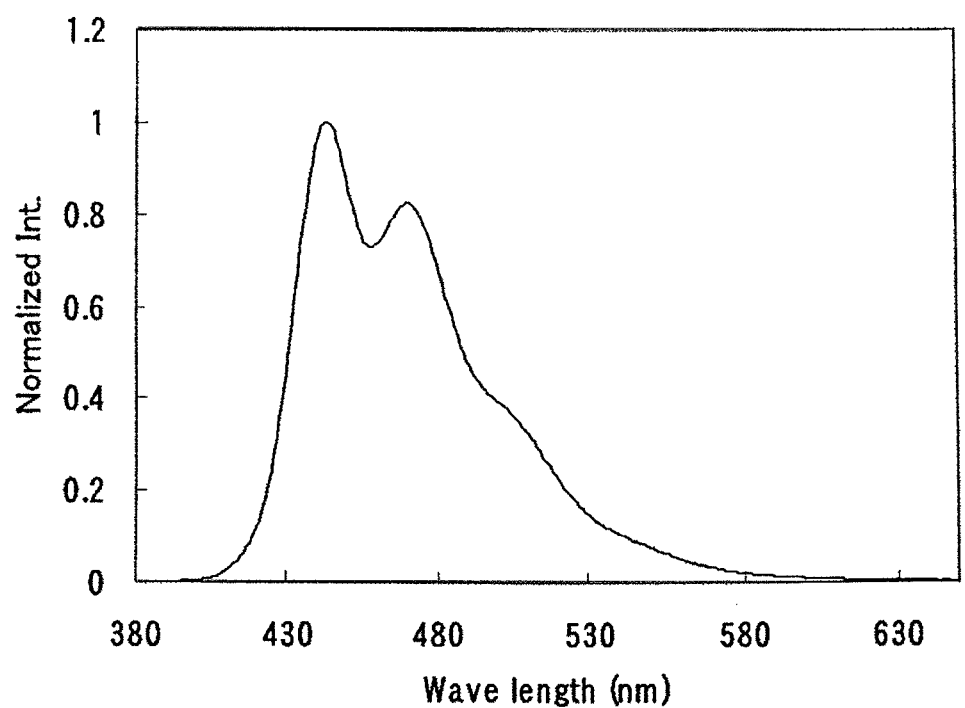
FIG. 4 is a view illustrating the EL spectrum of an organic light-emitting device produced in Example 4.

The characteristics of the obtained device were evaluated. Specifically, a voltage of 4.2 V was applied to the device while the ITO electrode (anode) was used as a positive electrode and the Al electrode (cathode) was used as a negative electrode. As a result, the device was observed to emit blue light with a light emitting efficiency of 6.9 cd/A. In addition, the blue light had CIE chromaticity coordinates of x=0.15, y=0.13. In addition, an EL spectrum of the organic light-emitting device produced in Example 4 was measured by using MCPD-7000 manufactured by Otsuka Electronics Co., Ltd. As a result, the EL spectrum shown in FIG. 4 was obtained.

Example 5

An organic light-emitting device was produced in the same manner as in Example 4 except that Exemplified Compound 26 was used instead of Exemplified Compound 48 as a guest of the light-emitting layer. When a voltage is applied to the device in the same manner as in Example 4, the device was observed to emit blue light.

As described above, an organic light-emitting device containing the indenopyrene compound of the present invention as the constitution material can emit light having good chromaticity with high luminance at a low applied voltage.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-285376, filed on Nov. 6, 2008 which is hereby incorporated by reference herein in its entirety.

The invention claimed is:

1. An indenopyrene compound represented by the Formula [2]:

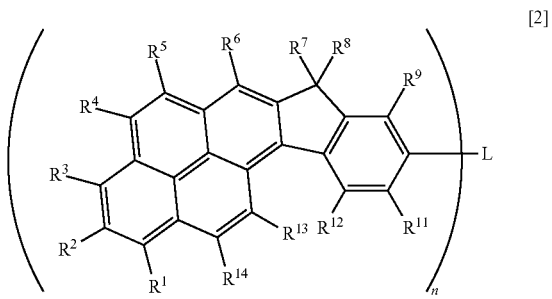

where:
n represents an integer of from 2 to 4; L represents a single bond or a substituent selected from a substituted or unsubstituted alkylene group, a substituted or unsubstituted alkenylene group, a substituted or unsubstituted alkynylene group, an n-valent substituted or unsubstituted aromatic group, an n-valent substituted or unsubstituted heterocyclic group, an n-valent substituted or unsubstituted fused polycyclic aromatic group, and an n-valent substituted or unsubstituted fused polycyclic heterocyclic group; $R^1$ to $R^9$ and $R^{11}$ to $R^{14}$ each independently represents a substituent selected from a hydrogen atom, a substituted or unsubstituted alkyl group, a substituted or unsubstituted alkenyl group, a substituted or unsubstituted alkynyl group, a substituted or unsubstituted aromatic group, a substituted or unsubstituted heterocyclic group, a substituted or unsubstituted fused polycyclic aromatic group, a substituted or unsubstituted fused polycyclic heterocyclic group, a halogen atom, and a substituted or unsubstituted amino group.

2. An indenopyrene compound according to claim 1, wherein:
$R^1$, $R^3$ to $R^5$, $R^9$, and $R^{11}$ to $R^{14}$ each represent a hydrogen atom; and
$R^2$, $R^6$, $R^7$, and $R^8$ each independently represents a hydrogen atom or a substituted or unsubstituted alkyl group.

3. An organic light-emitting device comprising:
an anode;
a cathode; and
an organic layer between the anode and the cathode, wherein:
one of the anode and the cathode is a transparent electrode or a semi-transparent electrode; and
at least one layer of the organic compound layer contains at least one kind of the indenopyrene compound according to claim 1.

4. An organic light-emitting device according to claim 3, wherein the indenopyrene compound is contained in a light-emitting layer.

5. An organic light-emitting device according to claim 4, wherein the light-emitting layer comprises a host and a guest.

6. An organic light-emitting device according to claim 3, wherein the indenopyrene compound is contained in an electron-injection layer or an electron-transporting layer.

7. An indenopyrene compound according to claim 1, wherein the compound is represented by the formula:
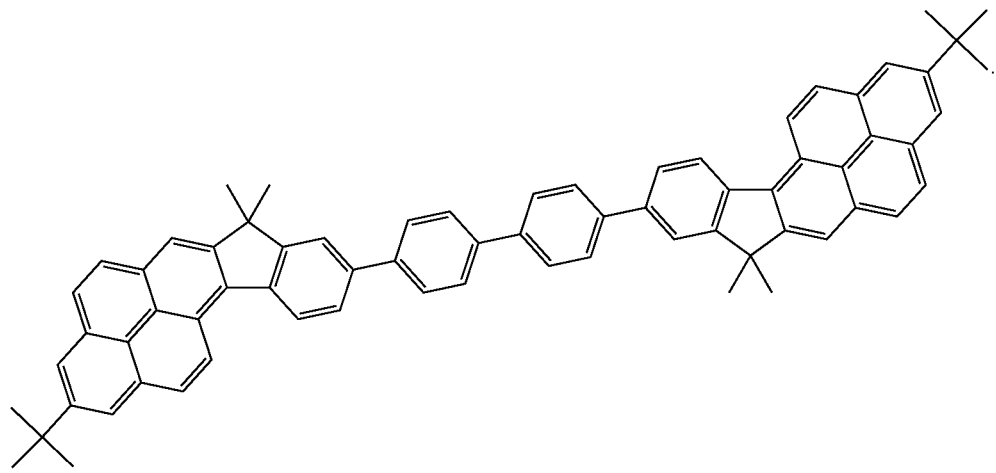 [SMILES: CC(C)(C)c1cc2ccc3cc4c(c5ccc(c1)c2c35)-c1ccc(-c2ccc(-c3ccc(-c5ccc6c(c5)C(C)(C)c5cc7ccc8cc(C(C)(C)C)cc9ccc(c5-6)c7c89)cc3)cc2)cc1C4(C)C]
* * * * *